United States Patent [19]

Niedballa et al.

[11] Patent Number: 5,275,801
[45] Date of Patent: Jan. 4, 1994

[54] 13,17-PROPIONIC ACID AND PROPIONIC ACID DERIVATIVE SUBSTITUTED PORPHYRIN COMPLEX COMPOUNDS, PROCESS FOR THEIR PRODUCTION AND PHARMACEUTICAL AGENTS CONTAINING THEM

[75] Inventors: Ulrich Niedballa; Heinz Gries; Jürgen Conrad; Ulrich Speck, all of Berlin, Fed. Rep. of Germany

[73] Assignee: Schering Aktiengesellschaft, Berlin and Bergkamen, Fed. Rep. of Germany

[21] Appl. No.: 392,328

[22] Filed: Aug. 11, 1989

[30] Foreign Application Priority Data

Aug. 13, 1988 [DE] Fed. Rep. of Germany ....... 3827940

[51] Int. Cl.$^5$ .................... A61K 49/00; C07D 487/22
[52] U.S. Cl. ........................ 424/1.65; 1.81; 540/145; 514/185; 424/9; 424/1.81; 436/173; 436/803; 128/653.4; 534/10; 534/15
[58] Field of Search .................. 534/10, 11, 12, 13, 534/15, 16; 424/1.1, 9; 540/145; 436/173, 803; 514/185, 410; 128/653

[56] References Cited

U.S. PATENT DOCUMENTS

| 4,849,207 | 7/1989 | Sakata et al. ............ 424/1.1 |
| 4,882,234 | 11/1989 | Lai et al. ............... 540/145 |
| 4,923,437 | 5/1990 | Gordon .................. 424/9 X |
| 4,977,177 | 12/1990 | Bommer et al. .......... 540/145 X |
| 4,986,256 | 1/1991 | Cohen et al. ............ 424/9 X |
| 5,156,840 | 10/1992 | Goers et al. ............ 424/85.91 |

FOREIGN PATENT DOCUMENTS

| B-45158/85 | 3/1986 | Australia . |
| B-48071/85 | 4/1986 | Australia . |
| B-64333/86 | 4/1987 | Australia . |
| 27687/89 | 6/1989 | Australia . |
| 0175617 | 3/1986 | European Pat. Off. . |
| 0213272 | 3/1987 | European Pat. Off. . |
| 0220686 | 5/1987 | European Pat. Off. . |
| 322198 | 6/1989 | European Pat. Off. ............ 540/145 |
| 350948 | 1/1990 | European Pat. Off. ...... A61K 49/00 |

OTHER PUBLICATIONS

Fuhrhop et al., "Hydrogen Evolution from Viologen Radicals and from Photochemically Reduced Tin(IV) Porphyrins in the Presence of Colloidal Platinum," Liebigs Ann. Chem., pp. 204–210 (1983).

Paquette et al., "Cinétique de la formation de la métalloporphyrine Cu(II)-dérivé tétra éthylènediamino de la protoporphyrine IX (ENP) en milieu aqueux," Canadian Journal of Chemistry, vol. 57, No. 22, pp. 2916–2922 (Nov. 15, 1979).

White et al., "A Homologous Series of Water-Soluble Porphyrins and Metalloporphyrins: Synthesis, Dimerization, Protonation and Self-Complexation," Bioinorganic Chemistry, vol. 4, No. 1, pp. 21–35 (Oct. 1971).

Kolski et al., "Temperature-Jump Investigation of the Kinetics of Imidazole Substitution on an Iron(III) Porphyrin in Aqueous Solution," Journal of the American Chemical Society 94:11, pp. 3740–3744 (May 31, 1972).

Nakajima et al., "Tumor Imaging with $^{111}$In Mono-DTPA-Ethylene-Glycol-Ga-Deuteroporphryn" Photochemistry and Photobiology, vol. 46, No. 5, pp. 783–788 (1987).

Primary Examiner—Robert L. Stoll
Assistant Examiner—John M. Covert
Attorney, Agent, or Firm—Millen, White, Zelano & Branigan

[57] ABSTRACT

Porphyrin complex compounds consisting of at least one porphyrin ligand, optionally at least one ion of an element of atomic numbers 5, 13, 21–32, 37–39, 42–44, 49, 50 or 57–83 as well as optionally cations of inorganic and/or organic bases, amino acids or amino acid amides, are valuable diagnostic media and therapeutic agents.

34 Claims, No Drawings

13,17-PROPIONIC ACID AND PROPIONIC ACID DERIVATIVE SUBSTITUTED PORPHYRIN COMPLEX COMPOUNDS, PROCESS FOR THEIR PRODUCTION AND PHARMACEUTICAL AGENTS CONTAINING THEM

BACKGROUND OF THE INVENTION

The invention relates to new porphyrin complex compounds with propionic acid or propionic acid derivative substituents in the 13 and 17 positions of the porphyrin skeleton, pharmaceutical agents containing these compounds, their use in diagnosis and therapy as well as processes for the production of these compounds and agents.

The use of complexing agents or complexes or their salts in medicine has been known for a long time. As examples there can be mentioned:

Complexing agents as stabilizers of pharmaceutical preparations, complexes and their salts as auxiliary agents for administration of poorly soluble ions (e.g., iron), complexing agents and complexes (preferably calcium or zinc), optionally as salts with inorganic and-/or organic bases, as antidotes for detoxification in the case of inadvertent incorporation of heavy metals or their radioactive isotopes and complexing agents as auxiliary agents in nuclear medicine with the use of radioactive isotopes such as $^{99m}Tc$ for scintigraphy are known.

In patent specifications EP 71564, EP 130934 and DE-OS 3401052 complexes and complex salts have recently been presented as diagnostic agents, mainly as NMR diagnostic agents.

These complexes and complex salts are quite well tolerated and guarantee a very complete excretion of ions. But they do not yet optimally meet all the criteria determining the relative effectiveness of an NMR contrast medium, of which above all there are to be mentioned: a great NMR activity (relaxivity), so that the contrast medium in the smallest possible concentrations lowers relaxation rates of the protons in tissue water and other nuclei relevant for NMR, such as phosphorus, fluorine and sodium, in vivo and thus makes possible locating tumors by increasing the signal intensity of the image obtained with the help of nuclear magnetic (spin) tomography; as selective concentration and/or retention of the contrast medium as possible on the target organ or cancerous tissue; adequate water solubility; great effectiveness; good compatibility; good chemical and biochemical stability.

The two first named points are especially relevant for imaging. Since the relaxation rates between the tissues differ at most only by the factor of 2–3 (T. E. Budinger and P. C. Lauterbur, Science 226, pp 288–298, 1984; J. M. S. Hutchinson and F. W. Smith in Nuclear Magnetic Resonance Imaging Edit. C. L. Partain et al., pp 231–249, Saunders, New York 1983) and the complexes and complexes salts of said patent specifications generally subject to the drawback that they are distributed only relatively unspecifically in the extracellular space and therefore are not always suitable for detection of pathologically changed tissue, there is a need especially for selectively binding, tumor-specific compounds which can be used in diagnosis.

It has been known for some years that porphyrin derivatives selectively concentrate in human and animal tumors (D. Kessel and T. H. Chou, Cancer Res. 43, pp 1994–1999, 1983, P. Hambright, Bioinorg. Chem. 5, pp 87–92, 1975; R. Lipson et al., Cancer 20, pp 2250–2257, 1967; D. Sanderson et al., Cancer 30, pp 1368–1372, 1972). First attempts to use this class of compounds as diagnostic agents have also been described (J. Winkelmann et al., Cancer Research 27, pp 2060–2064, 1967; N. J. Patronas et al., Cancer Treatment Reports 70, pp 391–395, 1986). With these compounds only the manganese(III) ion has proved suitable as a paramagnetic metal.

But the compounds described up to now are far from satisfactorily meeting the above criteria; their inadequate concentration in the target organ still requires special attention. An improvement of this property should, at the same time, help reduce the existing problems with toxicity and tolerability of previously known compounds.

For tumor imaging with radioisotopes, derivatives of deuteroporphyrin were recently proposed which contain, as additional complexing groups, polyaminopolycarboxylic acids bonded by ethylene glycol bridges on the porphyrin skeleton (Photochemistry and Photobiology Vol. 46, pp 783–788 (1987)). But such porphyrin esters are not very suitable for a parenteral use on patients—especially for NMR diagnosis, since the injection solutions obtainable from them because of hydrolytic cleavages are neither heat-sterilizable nor storable over a sufficient period.

Therefore there continues to be a need, for many purposes, for complex compounds, that are stable, easily soluble, but also better tolerated, more selectively binding, easily accessible over a considerable chemical variation range of substituents (which, e.g., makes possible the incorporation of metals other than manganese or several, also different, metals and thus at the same time also leads to a control of the properties and uses of the compounds) and which are suitable for diagnosis and-/or also therapy of tumors.

SUMMARY OF THE INVENTION

This invention makes available these compounds and pharmaceutical agents, and provides a process for their production.

It has been found that porphyrin complex compounds consisting of at least one porphyrin ligand, optionally of at least one ion of an element of atomic numbers 5, 13, 21–32, 37–39, 42–44, 49, 50 or 57–83 as well as optionally cations of inorganic and/or organic bases, amino acids or amino acid amides, surprisingly are outstandingly suitable for production of NMR, X-ray, photo and radio diagnostic agents, as well as photo and radio therapeutic agents.

Preferred complex compounds according to the invention exhibit as porphyrin ligands compounds of general formula I

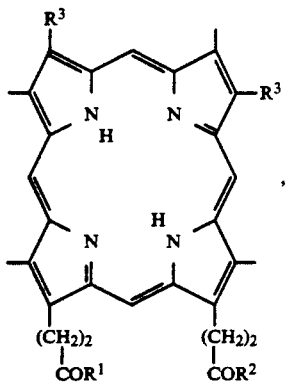

in which
R$^1$ and R$^2$ each independently mean an OH or (NH)$_x$-[Q-(NH)$_y$]$_w$-W group, x and y each independently mean the numbers 0, 1 or 2, w means the numbers 0 or 1, Q means C$_0$–C$_{20}$ hydrocarbylene group, W means a hydrogen atom or the group V-K, and V means straight-chain, branched, saturated or unsaturated C$_0$–C$_{20}$ hydrocarbylene groups optionally substituted by hydroxy, mercapto, imino, epoxy, oxo, thioxo, and/or NHK group(s), optionally containing imino, polyethylenoxy, phenylenoxy, phenylenimino, amido, hydrazido, ester group(s), oxygen, sulfur and/or nitrogen atoms, K means a hdyrogen atom or a complexing agent of general formulas IA, IB, IC or ID,

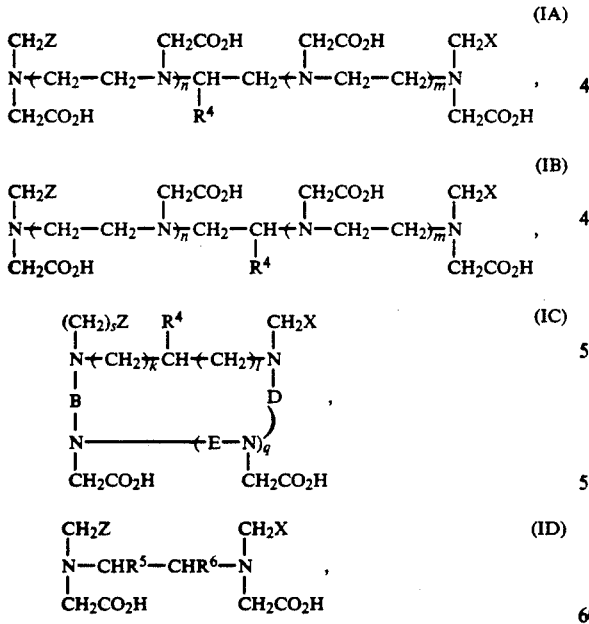

provided that either Z or R$^4$ is bonded on V, and n and m each stand for the numbers 0, 1, 2, 3 or 4, and n and m together add to no more than 4, k stands for the numbers 1, 2, 3, 4 or 5, l stands for the numbers 0, 1, 2, 3, 4 or 5 q stands for the numbers 0, 1 or 2, s stands for the numbers 0 or 1,

B, D and E, which are the same or different, in each case stand for the group

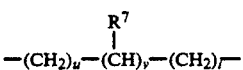

with

R$^7$ meaning hydrogen or a straight-chain, branched, saturated or unsaturated C$_1$–C$_{20}$ hydrocarbyl group optionally substituted by hydroxy and/or amino group(s) and optionally containing oxygen and/or nitrogen atom(s)

u means the numbers 0, 1, 2, 3, 4 or 5, v means the numbers 0 or 1, and

B, D and E each contain at least 2 and at most 5 carbon atoms,

Z stands for the radical —CO$_2$H or the group

X stands for the radical —CO$_2$H or

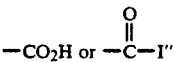

with

I" meaning another porphyrin ligand of general formula I, and the radical W contained in R$^1$ and R$^2$ stands here for a direct bond, R$^4$ stands for a direct bond or a hydrogen atom, R$^5$ and R$^6$ together stand for a dimethylene- or trimethylene-methine group optionally substituted by 1-2 hydroxy or 1-3 C$_1$–C$_4$ alkyl groups (if Z stands for the radical —CO$_2$H) or together stand for a trimethylene or tetramethylene group optionally substituted by 1-2 hydroxy or 1-3 C$_1$–C$_4$ alkyl groups (if Z stands for the group

provided that x and w do not stand at the same time for the number 0 when V is a C$_0$ alkylene chain; and that Z then stands only for

if R$^4$ at the same time means a hydrogen atom, and that Z then stands only for the radical —CO$_2$H, if R$^4$ at the same time means a direct bond and s the number 1;

each R$^3$ independently means the radical —CH(R$^1$')CH$_3$ or —CH$_2$CH$_2$R$^1$', wherein R$^1$' is an R$^1$ group provided that R$^1$, R$^2$ and R$^1$' do not simultaneously stand for the hydroxy group, and that optionally a portion of the CO$_2$H groups is present as ester and/or amide groups, and the hydroxy group in the 3 and/or 8 position is optionally present as ether or ester groups.

The $C_0$ alkylene group is understood to be a direct bond.

The complex compounds according to the invention comprise altogether four groups of compounds: a) compounds that contain no metal ion; b) compounds that contain a metal ion in the porphyrin ligand; c) compounds that contain at least one metal ion in the complexing agent radical K; and d) compounds that contain metal ions bonded both in the porphyrin ligand and in the complexing agent radical K, and the metal ions can be different.

For the use of the agents according to the invention in photo diagnosis and therapy, complex compounds that contain no metal ion are preferably used.

If the agents according to the invention are intended for use in NMR diagnosis, paramagnetic metal ions must be present in the complex. They are especially the divalent and trivalent ions of the elements of the atomic numbers 21-29, 42, 44, 57-70. Suitable ions are, for example, the chromium(III), manganese(II), manganese(III), iron(II), cobalt(II), nickel(II), copper(II), praseodymium(III), neodymium(III), samarium(III) and ytterbium(III) ion. The gadolinium(III), terbium(III), dysprosium(III), holmium(III), erbium(III) and iron(III) ions are especially preferred because of their high magnetic moment.

For the use of the agents according to the invention in nuclear medicine the metal ions must be radioactive. Radioisotopes of the elements copper, cobalt, gallium, germanium, yttrium, strontium, technetium, indium, ytterbium, gadolinium, samarium, thallium and iridium, for example, are suitable.

It is also possible for the radioactive isotope to be complexed from the porphyrin ligand ((case b) see above), or from complexing agent radical K (case c) or for it to be chelated from complexing agent radical K, while at the same time the porphyrin ligand contains another metal ion, for example manganese(III) (case d). If the media according to the invention are intended for use in X-ray diagnosis, at least one metal ion in the complex must be derived from an element of a higher atomic number to achieve a sufficient absorption of the X-rays. It has been found that for this purpose, diagnostic media that contain a physiologically compatible complex salt with central ions of elements of atomic numbers between 21-29, 42, 44, 57-83 are suitable; they are, for example, the lanthanum(III) ion and the above-named ions of the lanthanide series.

An essential advantage of the metal complexes according to the invention containing the complexing agent radical K is that with them the diagnostic or therapeutic effect produced by the metal ion can be further intensified by the incorporation of another metal ion, or by the incorporation of another metal ion different from the first one, especially the physical properties can be improved by an intensification of the magnetic effects and/or of the X-ray adsorption of the complex compounds.

In this case it is surprising that the essential properties determining the effectiveness of these pharmaceutical agents, such as, for example, especially the high selectivity and concentration of the complexes, are maintained or improved.

With the help of the complex compounds according to the invention surprisingly not only tumor tissues and individual organs, such as, for example, liver and kidneys, but also blood vessels can be represented without the use of special pulse sequences in vivo, as a result of which they can be used, among others, as perfusion agents.

As an example for the ions bound in the porphyrin skeleton there can be mentioned the metals aluminum, manganese, iron, cobalt, nickel, copper, zinc, gallium, technetium, indium, tin and thallium. Preferred are the metals aluminum, cobalt, zinc, gallium, technetium, indium, tin and especially manganese.

As examples for the ions bonded on the porphyrin skeleton there can be mentioned the transition metals, the rare earths and boron.

The hydrocarbylene group standing for V, Q or the hydrocarbyl group standing for $R^7$ can be straight-chain, branched, cyclic, aliphatic, aromatic or arylaliphatic, have up to 20 carbon atoms and, in the case of V, optionally contain —NH—, —O—, —S—, —N—, —CO—O—, —O—CO—, (O—CH$_2$CH$_2$—)poly, —NH—CO—, —CO—NH—, —NH—NH—, —C$_6$H$_4$—NH—, —C$_6$H$_4$—O—, —C$_6$H$_4$—, exhibit structures such, e.g., —CO—CH—(NH$_2$)—CH$_2$NH—, —S—(CH$_2$(2—NH— or be substituted by hydroxy, mercapto, imino, epoxy, oxo, thioxo and/or —NHK— groups. Straight-chain mono- to deca-methylene groups as well as $C_1$-$C_4$ alkylenephenyl(ene) groups are preferred.

As illustration, the following groups can be mentioned:
—(CH$_2$)$_2$NH—; —CH$_2$—O—C$_6$H$_4$—CH$_2$—; —CH$_2$—CH(OH)—CH$_2$—O—C$_6$H$_4$—CH$_2$—; —C(=NH)—)—O—C$_6$H$_4$—CH$_2$—; —(CH$_2$)$_4$—NH—CO—CH$_2$—O—C$_6$H$_4$—CH$_2$—; —(CH$_2$)$_4$—NH—CH$_2$—CH(OH)—CH$_2$—O—C$_6$H$_4$—CH$_2$—; —(CH$_2$)$_3$—O—C$_6$H$_4$—CH$_2$; —CH$_2$—CO—NH—(CH$_2$)$_3$—O—CH$_2$—; —CH$_2$—CO—NH—NH—; —CH$_2$—CO—NH—(CH$_2$)$_2$—; —CH$_2$—CO—NH(CH$_2$)$_{10}$—; —CH$_2$—CO—NH—(CH$_2$)$_2$—S—; —(CH$_2$)$_4$—NH—CO—(CH$_2$)$_8$; —CH$_2$—CO—NH—(CH$_2$)—NH; —(CH$_2$)$_3$—NH—; —(CH$_2$)NH—C(=S)—NH—C$_6$H$_4$—CH$_2$—; —CO—CH(NHK)—CH$_2$NHK—; —CH(CH$_3$)—S—(CH$_2$)$_2$—NH—; —(CH$_2$)$_2$NH—CO—CH$_2$—(OCH$_2$CH$_2$)$_{43}$OCH$_2$. See also, e.g., U.S. Application Serial No. 07/317,218.

As examples for the complexing agent radicals K there can be mentioned those of ethylenediaminetetraacetic acid, diethylenetriaminepentaacetic acid, trans-1,2-cyclohexane-diaminetetraacetic acid, 1,4,7,10-tetraazacyclododecane-tetraacetic acid, 1,4,7-triazacyclononanetriacetic acid, 1,4,8,11-tetraazatetradecanetetraacetic acid and 1,5,9-triazacyclododecanetriacetic acid, which are bonded on the respective porphyrin derivatives by (each containing in K) a carbon atom or a carbonyl group. Optionally a part of the carboxylic acids can be present as ester and/or amide.

The hydroxy groups contained in $R^3$ can optionally be present in etherified or esterified form, and hydrocarbons with 1-6, preferably 1-4 C atoms, such as, for example, methyl, ethyl, propyl, isopropyl. n-, sec- or tert-butyl, isobutyl, pentyl, hexyl, cyclohexyl and phenyl radicals are suitable as the alkyl substituent on the ether.

The acyl, for example, alkanoyl substituent on the ester can be those with 1-10 C atoms, e.g., formyl, acetyl, propionyl, isopropionyl, butyryl, isobutyryl, valenyl, benzoyl, trifluoroacetyl, mono-, di- and trichloroacetyl and nicotinyl radical are suitable, and the acetyl and benzoyl radical are preferred.

The remaining acidic hydrogen atoms, i.e., those which are not substituted by the metal ion(s), can optionally be replaced by cations of inorganic and/or organic bases, amino acids or amino acid amides or the corresponding acid groups can be converted wholly or partially into esters, preferably those with 1 to 7 C atoms, or amides, whose nitrogen atom can be substituted by one or two carbon radical(s)—which can be substituted in a straight-chain or branched-chain, cyclic, saturated or unsaturated manner, optionally by one or more hydroxy or $C_1$-$C_4$ alkoxy groups—with up to 10 carbon atoms. Suitable inorganic cations are, for example, the lithium ion, potassium ion, calcium ion and especially sodium ion. Suitable cations of organic bases are, among others, those of primary, secondary or tertiary amines, for example, ethanolamine, diethanolamine, morpholine, glucamine, N,N-dimethylglucamine and especially N-methylglucamine. Suitable cations of amino acids are for example those of lysine, arginine and ornithine as well as the amides of otherwise acidic or neutral amino acids.

The production of the complex compounds according to the invention takes place in that in porphyrins of general formula I'

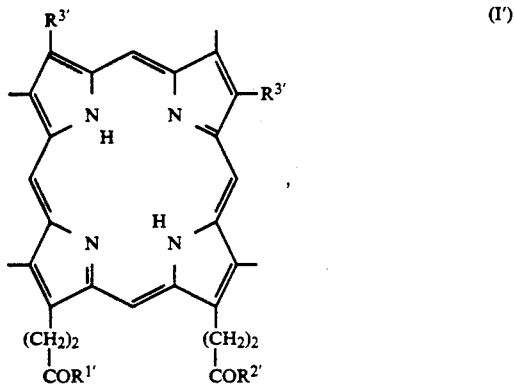

wherein $R^{1'}$ and $R^{2'}$ each stand for the OH— or O—$C_1$-$C_6$ alkyl group and $R^{3'}$ stands for the radical —CH(U)CH$_3$ or —CH$_2$CH$_2$—U with U meaning an OH— or O-$C_1$-$C_6$ alkyl group or a nucleofuge Nf in a way known in the art, optionally repeated, are reacted with compounds of general formula II

in which

Y stands for a hydrogen atom, for Nf or protecting group and $V^1$ stands for V (if $V^2$ stands for a $C_0$ alkylene chain, see below), or together with $V^2$ (see below) stands for V, and then, optionally after cleavage of the protecting groups, optionally a) the pyrrolic NH's can be substituted by the desired metal atom, optionally still present protecting groups are removed and then optionally the radical $V^2$-K, in which $V^2$ stands for V or for an activated form of V (if $V^1$ stands for a $C_0$ alkylene chain) or together with $V^1$ stands for V, is introduced, and then, optionally is reacted with at least one metal oxide or metal salt of an element of atomic numbers 21-32, 37-39, 42-44, 49, 50 or 57-83 or b) the substituent $V^2$-K, in which $V^2$ stands for V or for an activated form of V (if $V^1$ stands for a $C_0$ alkylene chain) or together with $V^1$ stands for V, can be introduced, optionally is reacted with at least one metal oxide or metal salt of an element of atomic numbers 21-32, 37-39, 42-44, 49, 50 or 57-83 and then optionally the pyrrolic NH's can be substituted by a metal atom or c) the substituent $V^2$-K, in which $V^2$ stands for V or for an activated form of V (if $V^1$ stands for a $C_0$ alkylene chain) or together with $V^1$ stands for V, can be introduced, the pyrrolic NH's optionally are substituted by a metal atom and then optionally reacted with at least one metal oxide or metal salt of an element of atomic numbers 21-32, 37-39, 42-44, 49, 50 or 57-83, and for the rings, 2 moles of the porphyrin, obtained after reaction of I' with II, is reacted with a complexing agent K, which contains two $V^2$ radicals, and optionally then acidic hydrogen atoms, still present in the complex compounds obtained according to a), b) or c), are substituted by cations of inorganic and/or organic bases, amino acids or amino acid amides, or the corresponding acid groups are converted wholly or partially into esters and/or amides and/or hydroxy groups present are converted into ethers or esters.

$V^1$ and $V^2$ together yield the radical V, and both $V^1$ and $V^2$ can stand for a $C_0$ alkylene chain.

Suitable protecting groups are, e.g., the carbobenzoxy and the t-butoxycarbonyl radical. Cl, Br, $CH_3C_6H_4SO_3$, $CH_3SO_3$ or the N-oxysuccinimide radical can be used as nucleofuge (Nf).

The functionalizing of the C-13 and/or C-17 propionic acid side chains to aminoalkylene substituted porphyrin C-13 and/or C-17 amide derivatives (which can be used as starting material for porphyrin complexes, which contain the complexing agent radical K) can take place by reaction of porphyrins carrying desired propionic acid chains (optionally in the form of activated porphyric acid derivatives such as, e.g., ester, anhydride or acid chloride) with optionally substituted hydrazines or with terminal alkylenediamines (optionally containing other also protected amino groups), wherein an amino group is protected, e.g., in the form of the carbobenzoxy and t-butoxycarbonyl radical. Removal of the protecting groups then can take place according to methods known in the literature, for example, by hydrogenation or treatment with trifluoroacetic acid or with hydrochloric acid/glacial acetic acid. The desired hydrocarbylene chain V can also be incorporated by steps into the porphyrin skeleton, e.g., first by amidation reaction with a partially protected diamine, cleavage of the protecting group and reaction with another compound of general formula II containing a nucleofuge group, e.g., with a di-t-butoxycarbonyl-protected 2,3-diaminopropionic acid, whose acid group is activated in the form of the hydroxy succinimide ester.

In functionalizing the C-13 propionic acid side chain in each case the corresponding isomeric C-17 also results with it.

Production of the porphyrin compounds functionalized in the 3 and 8 positions according to the invention can take place in a way known in the art first by conversion of the corresponding hydroxy compounds into compounds of general formula I', in which U stands for a nucleofuge such as, e.g., Br. Then reaction with compounds of general formula II, e.g., protected mono-, diamine- or also mercaptoalkylamines produces the porphyrin complexes suitable for introduction of the complexing agent radical K.

For introduction of complexing agent radical K the obtained compounds in a way known in the art can be reacted with isothiocyanatobenzyl substituted complexing agents (O. Gansow et al., Inorg. Chem. 25, 2772, 1986), amidated, hydrazinated (Houben-Weyl, Methoden der organischen Chemie [Methods of Organic Chemistry, vol. VIII/3 Georg Thieme Verlag, Stuttgart (1952), 654 and 675), acylated (J. March., Advanced Organic Chemistry, McGraw-Hill, 2nd ed., (1977) 377-382) and/or alkylated (Houben-Weyl, Methoden der organischen Chemie, vol. VI/3 Georg Thieme Verlag, Stuttgart (1965), 187).

Compounds of general formulas I'A, I'B, I'C, I'D, I"AB, I"C and I"D can be used as substrate for introduction of the units $V^2$ K:

In the last named case (I"C with s=O and Z"=H) the compounds of general formula I"C are reacted with activated porphyric acid derivatives.

As an example for an activated carboxyl group there can be mentioned anhydride (this can also be formed with the adjacent acid group of the same molecule), p-nitrophenyl acid ester and acid chloride.

Suitable as acid protecting groups Y' are lower alkyl, aryl and aralkyl groups, for example, methyl, ethyl, propyl, butyl, phenyl, benzyl, diphenylmethyl, triphenylmethyl, bis-(p-nitrophenyl)-methyl group, as well as trialkylsilyl groups.

Cleavage of protecting groups Y' can take place according to processes known to one skilled in the art, for example, by hydrolysis, alkaline saponification of esters with alkali in aqueous-alcoholic solution at temperatures of 0° C. to 50° C. or in case of tert-butyl esters with the help of trifluoroacetic acid.

The alkylation or acylation performed for introduction of the complexing agent units can be performed

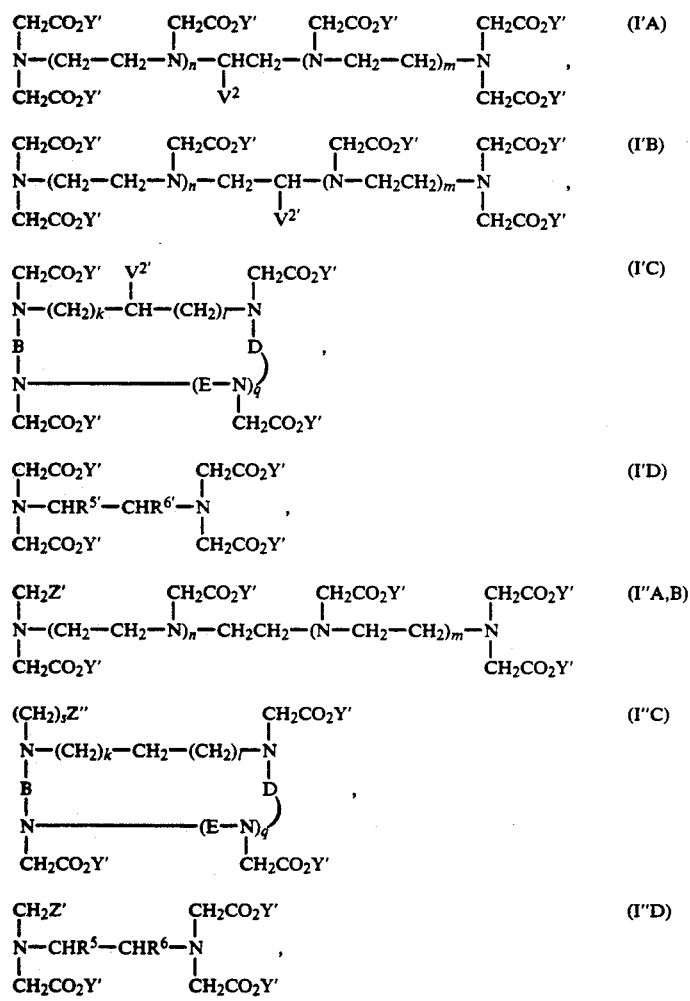

in which $V^{2'}$ stands for a substituent to be converted into Vhu 2, $R^{5'}$ and $R^{6'}$ stand for $R^5$ and $R^6$, which contain the substituent $V^{2'}$, Y' stands for a hydrogen atom or a acid protecting group, Z' stands for an activated carboxyl group and Z" stands for Z' or in case of s=0 for hydrogen, and wherein n, m, k, l, q, s, B, D, E, $R^7$, u and v have the meanings given in formula I.

with reagents, which contain the desired K-V substituent (bonded on a leaving group) or from which the desired substituent, optionally after modification by secondary reaction(s), is generated by the reaction. As examples for the first named there can be mentioned halides, mesylates, tosylates and anhydrides. For example, oxiranes, thiiranes, aziranes, α,β-unsaturated carbonyl compounds or their vinylogs, aldehydes, ketones, isothiocyanates and isocyanates belong to the second group.

As examples for secondary reactions there can be named hydrogenations, esterifications, oxidations, etherifications and alkylations, which are performed according to literature processes known to one skilled in the art.

In this way, porphyrin complexes are obtained, which, besides a metal in the porphyrin ring system, can stably bind other (same or different type) metals by the complexing agent K in the slightly hydrolyzable peripheral side chains.

If compounds are to be synthesized with two porphyrin rings in the molecule, either a porphyrin of general formula I, in which W stands for a hydrogen atom, is reacted with an optionally activated acid group of a K-containing porphyrin or 2 moles of a porphyrin of general formula I containing the radical (NH)$_x$-[Q-(NH)$_y$]$_w$-V$^1$-H are reacted with a bifunctionalized substrate of general formula I″A,B, I″C or I″D (e.g., bisanhydride).

Compounds I′ necessary as starting materials are known (e.g., European patent application publication No. 0154788) or can be produced from the corresponding polyamines (and functional groups present are optionally protected) by alkylation with an ester of general formula III

  Hal$CH_2COOY'$ (III)

in which Hal stands for chlorine, bromine or iodine.

The reaction takes place in polar aprotic solvents such as, for example, dimethylformamide, dimethyl sulfoxide or hexamethylphosphoric acid triamide in the presence of an acid catcher, such as, for example, tertiary amine (for example, triethylamine, trimethylamine, N,N-dimethylaminopyridine, 1,5-diazabicyclo[4.3.0]-nonene-5 (DBN), 1,5-diazabicyclo[5.4.0]-undecene-5 (DBU), alkali carbonate, alkaline-earth carbonate or bicarbonate (for example, sodium, magnesium, calcium, barium, potassium carbonate and bicarbonate) at temperatures between −10° C. and 120° C., preferably between 0° C. and 50° C.

Production of activated carboxyl derivatives I″A,B, I″C or I″D (e.g. mixed anhydride, N-hydroxysuccinimide esters, acylimidazoles, trimethylsilyl esters) takes place according to methods known in the literature [Houben-Weyl, Methoden der organischen Chemie [Methods of Organic Chemistry], Georg Thieme Verlag, Stuttgart vol. E 5 (1985), 633; Org. React. 12, 157 (1962)] or is described in the experimental part.

The corresponding polyamines necessary as starting materials for the production of the polyamine polyacids of general formula I′A are produced analogously to methods known in the literature (for example, Canad. Patent No. 1 178 951, Eur. I. Med. Chem.-Chim.Ther. 1985, 20, 509 and 1986, 21, 333), by starting from amino acids which are converted into optionally ethylenamine substituted amides (for example, with N-(2-aminoethyl)-carbamic acid benzyl ester) and then reduced (optionally after cleavage of the protecting groups) to the desired amines (preferably with diborane or lithium aluminum hydride).

If it is desired to synthesize the polyamine starting materials for the compounds of general formula I′B, it is necessary, before the reduction, to substitute such an amide on the α-amino group by reaction with, for example, ethyloxamate in a polar solvent such as, for example, tetrahydrofuran, dimethyl sulfoxide or dimethoxyethane at a temperature between 50° C. and 250° C., preferably 70° C. to 150° C. (optionally in a pressure vessel), so that a 3-aza-2-oxo-glutaric acid diamide derivative is obtained as intermediate product.

Production of the cyclic polyamides necessary as starting materials for I′C or I″C takes place by cyclization of two reagents, of which (in the case of synthesis of I′C) the one is V$^2{'}$ substituted.

The cyclization is performed according to methods known in the literature, for example, Org. Synth. 58, 86 (1976), Macrocylic Polyether Syntheses, Springer Verlag, Berlin, Heidelberg, New York 1982, Coord. Chem. Rev. 3, 3 (1968), Ann. Chem. 1976, 916: one of the two reagents carries on the chain end two leaving groups, the other two nitrogen atoms, which nucleophilically displace these leaving groups. As an example there can be mentioned the reaction of terminal dibromo, dimesyloxy, ditosyloxy or dialkoxy carbonyl alkylene compounds optionally containing one or two nitrogen atom(s) with terminal diazaalkylene compounds optionally containing one or two additional nitrogen atom(s) in the alkylene chain, of reagents is V$^2{'}$ substituted.

The nitrogen atoms are optionally protected, for example, as tosylates, and are released before the subsequent alkylation reaction according to processes known in the literature.

If diesters are used in the cyclization reaction, the diketo compounds thus obtained must be reduced according to processes known to one skilled in the art, for example, with diborane.

As substituent V$^2{'}$, which can be converted into V$^2$, hydroxy, and nitrobenzyl, hydroxy and carboxyalkyl as well as thioalkyl radicals with up to 20 carbon atoms are suitable, among others. They are converted according to processes known in the literature to one skilled in the art (Chem. Pharm. Bull. 33, 674 (1985), Compendium of Org. Synthesis, Vol. 1-5, Wiley and Sons, Inc., Houben-Weyl, Methoden der organischen Chemie [Methods of Organic Chemistry], Vol. VIII, Georg Thieme Verlag, Stuttgart, J. Biochem. 92, 1413, 1982) into the desired substituents (for example with the amino, hydrazino, hydrazinocarbonyl, epoxide, anhydride, halo, halocarbonyl, mercapto, isothiocyanate group as functional group), and in the case of the nitrobenzyl radical first a catalytic hydrogenation (for example, according to P. N. Rylander, Catalytic Hydrogenation over Platinum Metals, Academic Press 1967) to the aminobenzyl derivative must be performed.

Examples for the conversion of hydroxy or amino groups bound on aromatic or aliphatic radicals are the reactions—performed in anhydrous aprotic solvents such as tetrahydrofuran, dimethoxyethane or dimethyl sulfoxide in the presence of an acid trap such as, for example, sodium hydroxide, sodium hydride or alkali or alkaline-earth carbonates such as, for example, sodium, magnesium, potassium, calcium carbonate at temperatures between 0° C. and the boiling point of the respective solvent, but preferably between 20° C. and 60° C.—with a substrate of general formula IV

 Nf-L-Fu (IV)

in which Nf stands for a nucleofuge such as, e.g., Cl, Br, I, $CH_3C_6H_4SO_3$ or $CF_3SO_3$, L stands for an aliphatic, aromatic, arylaliphatic, branched, straight-chain or cyclic hydrocarbon radical with up to 20 carbon atoms and Fu for the desired terminal functional group, optionally in protected form (DE-OS 34 17 413).

As examples for compounds of general formula IV there can be mentioned $Br(CH_2)_2NH_2$, $Br(CH_2)_3OH$, $BrCH_2COOCH_3$, $BrCH_2CO_2{}^tBu$, $ClCH_2CONHNH_2$, $Br(CH_2)_4CO_2C_2H_5$, $BrCH_2COBr$, $ClCH_2COOC_2H_5$, $BrCH_2CONHNH_2$,

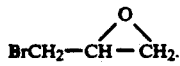

Conversions of carboxy groups can be performed, for example, according to the carbodiimide process (Fieser, Reagents for Organic Syntheses 10, 142), by a mixed anhydride [Org. Prep. Proc. Int. 7.215(1975)] or by an activated ester (Adv. Org. Chem. Part B, 472).

Production of the amines necessary as starting substances for cyclization takes place analogously to methods known in the literature.

Starting from an N-protected amino acid, a triamine is obtained by reaction with a partially protected diamine (for example, according to the carbodiimide method), cleavage of the protecting groups and diborane reduction.

Reaction of a diamine obtainable from amino acids (Eur. J. Med. Chem.-Chim. Ther. 21, 333 (1986)) with a double molar amount of an N-protected omega-amino acid yields a tetramine after suitable working up.

In both cases the number of carbon atoms between the N atoms can be determined by the type of diamines or amino acids used as coupling reactants.

Introduction of the desires metals (e.g., Mn, Fe, Co, Ni, Cu, Zn, Ga, In, Tc, Sn, Sm, Eu, Gd, Tl) into the porphyrin ligands takes place according to methods known in the literature (The Porphyrins, ed. D. Dolphin, Academic Press, New York 1960, Vol. V, p. 459) by warming with the corresponding metal salts, preferably acetates, optionally with addition of acid-buffering agents such as sodium acetate. As solvents there are especially suitable polar solvents, such as, for example, chloroform, acetic acid, methanol, ethanol, dimethylformamide, water.

The complexing, to the extent possible, should be performed with the exclusion of light, since a photochemical decomposition of the porphyrins can take place. Preferred metals are manganese, iron, technetium, gallium and indium. If the complexing agent according to the invention contains radical K, the introduction of the porphyrin metal can take place before or after linkage of the complexing agent radical K as well as before or after chelating this complexing agent with one or more metal(s). As a result an especially flexible procedure for the synthesis of the compounds according to the invention is made possible so that, for example, metals with a short half-life, for example $^{111}In$, whether in the porphyrin ligands or in the complexing agents, can be introduced only in the last synthesis step.

Chelating of radical K can take place in the way disclosed in patent specification DE-OS 34 01 052, in that the metal oxide or a metal salt (for example, the nitrate, acetate, carbonate, chloride or sulfate) of the element of atomic numbers 21-32, 37-39, 42-44, 49, 57-83 is dissolved or suspended in water and/or a lower alcohol (such as methanol, ethanol or isopropanol) and is reacted with the solution or suspension of the equivalent amount of the complexing ligand and then, if desired, available acidic hydrogen atoms of the acid groups are substituted by cations of inorganic and/or organic bases or amino acids.

In this case, the neutralization takes place with the help of inorganic bases (for example, hydroxides, carbonates or bicarbonates) of., for example, sodium, potassium, lithium, magnesium or calcium and/or organic bases such as, among others, of primary, secondary or tertiary amines, such as, for example, ethanolamine, morpholine, glucamine, N-methyl and N,N-dimethylglucamine, as well as basic amino acids, such as, for example, lysine, arginine and ornithine or of amides of originally neutral or acid amino acids.

For the production of the neutral complex compounds, the desired bases can be added to the acidic complex salts in aqueous solution or suspension such that the neutral point is reached. The resulting solution can then be evaporated to dryness in a vacuum. It is often advantageous to precipitate the formed neutral salts by addition of water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus to obtain crystallizates easy to isolate and purify. It has proved particularly advantageous to add the desired base to the reaction mixture already during the complexing and thus to save a process step.

If the acid complex compounds contain several free acid groups, it is often useful to produce neutral mixed salts, which contain both inorganic and organic cations as counterions.

This can happen, e.g., in that the complexing ligand in aqueous suspension or solution is reacted with the oxide or salt of the element yielding the central ion and with half of the amount of an organic base necessary for neutralization, the formed complex salt is isolated, is optionally purified and then mixed with the amount of inorganic base necessary for complete neutralization. The sequence of addition of bases can also be reversed.

Another possibility for achieving neutral complex compounds consists in converting the remaining acid groups in the complex wholly or partially, for example, into esters or amides. This can takes place by subsequent reaction on the finished complex (e.g., by exhaustive reaction of the free carboxy groups with dimethyl sulfate) as also by use of a suitably derivatized substrate for introduction of the complexing agent units K-V² of general formulas I'A, I'B, I'C, I'D, I''AB, I''C, I''D (e.g., 3-ethoxy-carbonyl-methyl-6-[2-(2,6-dioxomorpholino-ethyl]-3,6-diazaoctanedioic acid.

In the case of use of complex compounds containing radioisotopes, their production can be performed according to the methods described in "Radiotracers for Medical Applications," Volume I, CRC-Press, Boca Raton, Fla.

Production of the pharmaceutical agents according to the invention also takes place in a way known in the art, in that the complex compounds according to the invention—optionally with addition of the additives usual in galenicals—are suspended or dissolved in aqueous medium and then the suspension or solution is optionally sterilized. Suitable additives are, for example, physiologically safe buffers (such as, for example, tromethamine), small additions of complexing agents (such as, for example, diethylenetriaminepentaacetic acid) or, if necessary, electrolytes such as, for example, sodium chloride or, if necessary, antioxidizing agents such as, for example, ascorbic acid.

If suspensions or solutions of the agents according to the invention in water or physiological salt solution are desired for enteral administration or other purposes, they are mixed with one or more of the auxiliary agent(s) usual in galenicals (for example, methylcellulose, lactose, mannitol) and/or surfactants (for example lecithins, Tween ®, Myrj ®) and/or aromatic substance(s) for flavoring (for example, essential oils).

In principle it is also possible to produce the pharmaceutical agents according to the invention without isolation of the complex salts. But in this case special care must be used to perform the chelating so that the salts and salt solutions according to the invention are practically free from noncomplexed toxically acting metal ions.

This can be guaranteed, for example, with the help of color indicators such as xylenol orange by control titration during the production process. The invention therefore also relates to processes for the production of the complex compounds and their salts. As a last safety measure, there remains a purification of the isolated complex salt.

The pharmaceutical agents according to the invention preferably contain 70 micromol/l to 70 mmol/l in the form of its complex salt and generally are dosed in amounts from 0.1 micromol to 1 mmol/kg of body weight. They are intended for enteral and parenteral application.

The complex compounds according to the invention are used:

1. for NMR and X-ray diagnosis in the form of their complex with the ions of the elements of atomic numbers 21–29, 42, 44, and 57–83;

2. for radiodiagnosis, radiotherapy and radiation therapy in the form of their complexes with the isotopes of the elements of atomic numbers 27, 29–32, 37–39, 43, 49, 62, 64, 70 and 77.

3. for photodiagnosis and phototherapy, preferably in the form of their metal-free porphyrins.

The agents according to the invention meet the various requirements for suitability as contrast agents for nuclear magnetic tomography. They are outstandingly suitable, after enteral or parenteral application, by increasing the signal intensity, for improving the image obtained with the help of nuclear magnetic tomography to convey information. Further, they exhibit the high efficacy that is necessary to burden the body with the smallest possible amounts of foreign substances and the good tolerability that is necessary to maintain the noninvasive character of the examinations.

The good water solubility of the agents according to the invention makes it possible to produce highly concentrated solutions to keep the volume load of the circulatory system in acceptable limits and balance the dilution by body fluid. Further, the agents according to the invention exhibit not only a high stability in vitro but also a surprisingly high stability in vivo, so that a release or an exchange of the ions—toxic in themselves—not covalently bonded in the complexes, within the time in which the new contrast media are again completely excreted, takes place only exceptionally slowly.

In general the media according to the invention for use as NMR diagnostic media are dosed in amounts of 5 micromol to 100 micromol/kg of body weight, preferably 50 micromol to 100 micromol/kg of body weight. Details of the use are discussed, for example, in H. J. Weinmann et al., Am. J. of Roentgenology 142, 619 (1984).

Especially low dosages (below 1 mg/kg of body weight) of organ-specific NMR diagnostic media can be used, for example, for detection of tumors and myocardial infarction.

Further, the complex compounds according to the invention are advantageously used as susceptibility reagents and as shift reagents for in vivo NMR spectroscopy.

The media according to the invention, because of their favorable radioactive properties and the good stability of the complex compounds contained in them are also suitable as radiodiagnostic agents. Details of their use and dosage are described, e.g., in "Radiotracers for Medical Applications," CRC-Press, Boca Raton, Fla.

Another imaging method with radioisotopes is positron emission tomography, which uses positron-emitting isotopes such as, for example, $^{43}$Sc, $^{44}$Sc, $^{52}$Fe, $^{55}$Co, $^{68}$Ga and $^{81}$Rb (W. D. Heis, M. E. Phelps, Positron Emission Tomography of Brain, Springer Verlag, Heidelberg, New York 1983).

The compounds according to the invention can also be used in radioimmunotherapy. The latter is distinguished from the corresponding diagnostic agent only by the amount and type of radioactive isotope used. The aim in this case is the destruction of tumor cells by high-energy shortwave radiation with the smallest possible range. The specificity of the complex according to the invention in this case is of decisive importance, since unspecifically localized complexes lead to destruction of healthy tissue.

At the target site the metal ion, selected because of its cell-killing properties, emits rays that lethally damage the cells. Suitable $\beta$-emitting ions are, for example, $^{46}$Sc, $^{47}$Sc, $^{48}$Sc, $^{72}$Ga and $^{73}$Ga. $\alpha$-emitting ions exhibiting suitable short half-lives are, for example, $^{211}$Bi, $^{212}$Bi, $^{213}$Bi and $^{214}$Bi, and $^{212}$Bi is preferred. A suitable photon and electron emitting ion is $^{158}$Gd, which can be obtained from $^{157}$Gd by neutron capture. A suitable isotope emitting $\alpha$-particles, after neutron capture, is $^{10}$B.

In the in vivo application of the therapeutic agents according to the invention, these can be administered with a suitable vehicle, such as, for example, serum or physiological salt solution and together with another protein such as, for example, human serum albumin. The dosage depends in this case on the type of cell destruction and the metal ion used.

The therapeutic agents according to the invention are applied parenterally, preferably intravenously.

Details of use of radiotherapeutic agents are discussed, for example, in R. W. Kozak et al. TIBTEC, October 1986, 262.

The agents according to the invention are also suitable as X-ray contrast agents, and it is especially to be stressed that, in comparison with iodine-containing contrast agents used so far they make it possible to detect pharmacokinetics that considerably promote diagnosis. Further, they are especially valuable because of the favorable absorption properties in the ranges of higher tube voltages for digital subtraction techniques.

Generally, the agents according to the invention are dosed for use as X-ray contrast media analogously, for example, to meglumine diatrizoate, in amounts of 100 micromol to 1 mmol/kg of body weight, preferably 300 micromol to 800 micromol/kg of body weight.

Details of the use of contrast media are discussed, for example, in Barke, Roentgenkontrastmittel [X-ray Contrast Media], G. Thieme, Leipzig (1970) and P. Thurn, E. Bucheler, Einfuehrung in die Roentgendiagnostik [Introduction to X-ray Diagnosis], G. Thieme, Stuttgart, New York (1977).

The compounds according to the invention are also especially suitable for photodiagnosis and phototherapy.

Until now this methodology has been affected by the drawback that in it can easily lead to damage to healthy tissue, caused by a nonspecific bonding of the porphyrin. By the high incorporation rate of the compounds according to the invention the dose used and thus the undesired phototoxic effect on healthy tissue can be prevented or at least reduced. In this case preferably metal-free porphyrins are used; they have the property of fluorescing during radiation with light of wavelengths of about 400 nm and thus to indicate the site of the tumor. With radiation with light of wavelength of about 630 nm, they release singlet oxygen, which destroys the tumor cells.

For use as photodiagnostic agents or phototherapeutic agents the agents according to the invention are generally dosed in amounts of 0.1 micromol to 5 micromol or 1 micromol to 20 micromol, preferably 0.5 micromol to 2.5 micromol or 2.5 micromol to 10 micromol/kg of body weight. They are applied parenterally, preferably intravenously.

Details of use of porphyrins as photodiagnostic agents and phototherapeutic agents are discussed, for example, in D. A. Cortese et al., Mayo Clin. Proc. 54:635-642, 1979; T. J. Dougherty, Cancer Res., 42:1188, 1982, T. J. Dougherty, Porphyrin Photosensitization, pp 3-13, New York, Plenum Publishing Corp. 1982; T. J. Dougherty et al., Cancer Res. 38:2628-2635, 1978.

A preferred compound of this invention is that of Example 28.

Altogether it has been possible to synthesize new complex compounds, which yield new possibilities in diagnostic and therapeutic medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application P 38 27 940.1, are hereby incorporated by reference.

In the following examples "Cld" means calculated and "Fnd" means found.

EXAMPLES

Example 1 a) N-(6-tert-butoxycarbonylamino-hexyl)-hematoporphyrin-IX-13-amide and b) N,N'-bis(6-tert-butoxycarbonylamino-hexyl)-hematoporphyrin IX 13,17-diamide 1.80 g (3 mmol) of hematoporphyrin IX, 810 mg (6 mmol) of 1-hydroxybenzotriazole, 1.52 g (6 mmol) of N-BOC-1,6-diaminohexane hydrochloride and 608 mg (6 mmol) of triethylamine are added to 300 ml of dimethylformamide. With stirring and covering with argon, it is cooled to −10° C. and mixed with 1.24 g (6 mmol) of dicyclohexylcarbodiimide. The solution is stirred for 1 hour at the low temperature and then permitted to warm to room temperature. The course of the reaction is followed by thin-layer chromatography. After 3 hours only residues of the starting material are present. The solution is now evaporated to dryness in an oil pump vacuum. The residue is dissolved in dichloromethane/acetone and washed with saturated sodium bicarbonate solution. The organic solution is dried on sodium sulfate and evaporated to dryness in a vacuum. The residue is separated by column chromatography on silica gel with isopropanol/methanol (0-100%) into the two title compounds. The diamide is eluted as first compound from the column.

| a) | Yield: 0.78 g (32.6% of theory) | | | | |
|---|---|---|---|---|---|
| | Analysis: | Cld: | C 67.82 | H 7.59 | N 10.54 |
| | | Fnd: | C 67.69 | H 7.76 | N 10.40 |
| b | Yield: 1.68 g (56.3% of theory) | | | | |
| | Analysis: | Cld: | C 67.58 | H 8.30 | N 11.26 |
| | | Fnd: | C 67.49 | H 8.41 | N 11.20 | c) N-(6-aminohexyl)-hematoporphyrin IX 13-amide 490 mg (0.6 mmol) of the monoamide produced under example 1a is dissolved in 7 ml of 2 molar hydrochloric acid in glacial acetic acid and stirred for one hour at room temperature with exclusion of moisture. Then no starting material could be any longer detected in the thin-layer chromatogram. It is evaporated to dryness in a vacuum, taken up in distilled water, subjected to freeze-drying and the title compound is obtained as trihydrochloride.

| Yield: 450 mg (93.0% of theory) | | | | | |
|---|---|---|---|---|---|
| Analysis: | Cld: | C 57.74 | H 6.66 | N 10.10 | Cl 12.78 |
| | Fnd: | C 57.59 | H 6.83 | N 9.88 | Cl 12.82 |

Example 2

N,N'-bis(6-aminohexyl)-hematoporphyrin IX 13,17-diamide 500 mg (0.5 mmol) of the diamide produced under example 1b is dissolved in 8 ml of 2 molar hydrochloric acid in glacial acetic acid and is treated analogously to the instruction for example 1c.

Yield: 400 mg (85% of theory)
Analysis: Cld:   C 58.22   H 7.50   N 11.91   Cl 15.07

| | | | | | |
|---|---|---|---|---|---|
| Fnd: | C 57.98 | H 7.63 | N 11.73 | Cl 15.26 | |

Example 3 a) N-(2-tert-butoxycarbonylamino-ethyl)-hematoporphyrin IX 13-amide b) N,N'-Bis(2-tert-butoxycarbonlyamino-ethyl)-hematoporphyrin IX 13,17-diamide 1.20 g (2 mmol) of hematoporphyrin IX, 540.5 mg (4 mmol) of 1-hydroxybenzotriazole, 576.9 mg (4 mmol) of N-(2-aminoethyl)-carbamic acid tert-butyl ester as well as 825.3 mg (4 mmol) of dicyclohexylcarbodiimide are reacted in 250 ml of dimethylformamide as described in example 1. Then the operation continues analogously to this instruction. Diamide b) is eluted first as nonpolar compound.

| 457 mg (30.9% of theory) of title compound a). | | | | |
|---|---|---|---|---|
| Analysis: | Cld: | C 66.47 | H 7.07 | N 11.34 |
| | Fnd: | C 66.32 | H 7.25 | N 11.24 |
| 967.9 mg (54.8% of theory) of title compound b) | | | | |
| Analysis: | Cld: | C 65.28 | H 7.53 | N 12.69 |
| | Fnd: | C 65.02 | H 7.80 | N 12.47 | c) N-(2-aminoethyl)-hematoporphyrin IX 13-amide 741 mg (1 mmol) of the monoamide described under example 3a) is dissolved in 10 ml of 2 molar hydrochloric acid in glacial acetic acid and reacted and worked up analogously to example 1c).

| Yield: 647.9 mg (86.6% of theory) | | | | | |
|---|---|---|---|---|---|
| Analysis: | Cld: | C 57.80 | H 6.06 | N 11.23 | Cl 14.22 |
| | Fnd: | C 57.66 | H 6.18 | N 11.14 | Cl 14.34 |

Example 4

N-(2-aminoethyl)-3,8-bis(2-hydroxyethyl)-deuteroporphyrin 13-amide

Analogously to the instruction for example 3a and 3c the title compound is obtained as trihydrochloride from 3,8-bis(2- hydroxyethyl)-deuteroporphyrin and N-(2-aminoethyl)-carbamic acid t-butyl ester and then cleavage of the BOC protecting group.

| Analysis: | Cld: | C 57.80 | H 6.06 | N 11.23 | Cl 14.22 |
|---|---|---|---|---|---|
| | Fnd: | C 57.46 | H 5.91 | N 11.10 | Cl 14.43 |

Example 5

N,N'-bis(2-aminoethyl)-hematoporphyrin-IX-13,17-diamide

In 12 ml of 2 molar hydrochloric acid in glacial acetic acid 883 mg (1 mmol) of the compound according to example 3b and analogously to example 1c is reacted and worked up. Thus a yield of 701 mg (84.8% of theory) of the title compound is obtained as tetrahydrochloride.

| Analysis: | Cld: | C 55.21 | H 6.34 | N 13.55 | Cl 17.15 |
|---|---|---|---|---|---|
| Fnd: | | C 55.06 | H 6.48 | N 13.44 | Cl 17.29 |

α) N-(2-benzyloxycarbonylaminoethyl)-hematoporphyrin IX 13-amide

β) N,N'-bis(2-benzyloxycarbonylaminoethyl)hematoporphyrin IX 13,17-diamide

In 300 ml of dimethylformamide 1.80 g (3 mmol) of hematoporphyrin IX, 810 mg (6 mmol) of 1-hydroxybenzotriazole, 1.38 g (6 mmol) of N-(2-aminoethyl)-carbamic acid benzyl ester hydrochloride, 608 mg (6 mmol) of triethylamine and 1.24 g (6 mmol) dicyclohexylcarbodiimide are reacted and worked up as described under example 1. The raw product is separated by column chromatography on silica gel with a mixture of ethanol with ammonia (25%) in a ratio of 98/2 in the components. The diamide is eluted as first compound from the column.

| α) | Yield: 0.52 g (22.4% of theory) | | | | |
|---|---|---|---|---|---|
| | Analysis: | Cld: | C 68.20 | H 6.50 | N 10.84 |
| | | Fnd: | C 67.97 | H 6.72 | N 10.69 |
| β) | Yield: 1.81 g (63% of theory) | | | | |
| | Analysis: | Cld: | C 68.19 | H 6.57 | N 11.78 |
| | | Fnd: | C 67.85 | H 6.78 | N 11.61 |

δ) N,N'-bis-(2-aminoethyl)-hematoporphyrin IX 13,17-diamide 599 mg (0.63 mmol) of the diamide produced according to β) is dissolved in 6 ml of trifluoroacetic acid and stirred for 12 hours at room temperature with exclusion of moisture. Then it is evaporated to dryness in a vacuum. The residue is dissolved in distilled water and chromatographed on silica gel. The product is eluted with isopropanol/aqueous ammonia solution. The combined eluates are concentrated by evaporation, filtered, taken up in water and freeze-dried. 333 mg (77.4% of theory) of the title compound is obtained at free amine.

| Analysis: | Cld: | C 66.84 | H 7.38 | N 16.41 |
|---|---|---|---|---|
| | Fnd: | C 66.93 | H 7.30 | N 16.25 |

Example 6

N,N'-bis(2-aminoethyl)-3,8-bis(2-hydroxyethyl)-deuteroporphyrin 13,17-diamide

Analogously to the instruction for example 3b and 5, the title compound is obtained at tetrahydrochloride from 3,8-bis(2- hydroxyethyl)-deuteroporphyrin and N-(2-aminoethyl)-carbamic acid t-butyl ester and then cleavage of the BOC protecting group.

| Analysis: | Cld: | C 55.21 | H 6.34 | N 13.55 | Cl 17.15 |
|---|---|---|---|---|---|
| | Fnd: | C 55.41 | H 6.29 | N 13.67 | Cl 17.03 |

Example 7 a) 5.0 g (35.6 mmol) of D,L-2,3-diaminopropionic acid monohydrochloride is suspended in 27 ml of water, mixed with 72 ml of tert-butanol and adjusted to pH 8.5 by addition of 37 ml of 0.5 n sodium carbonate solution. At the same time 32 g (142 mmol) of di-tert-butyl dicarbonate and 114 ml of 0.5 n sodium carbonate solution are instilled in the clear solution at pH 8.5 to 9. After stirring overnight, it is exhaustively extracted with hexane, the aqueous phase is brought to pH 4 by addition of 50 g of citric acid and exhaustively extracted with ethyl acetate. It is dried on sodium sulfate, evaporated to dryness and the residue is recrystallized from ethyl acetate/hexane. 9.0 g (83% of theory) of D,L-2,3-bis(-tert-butoxycarbonylamino)propionic acid with a melting point of 163°-164° C. is obtained.

b) 3.04 g (10 mmol) of the compound obtained under a) is dissolved in 50 ml of tetrahydrofuran. With cooling to −12° C. 1.21 g (12 mmol) of triethylamine is instilled and then 1.66 g (12 mmol) of chloroformic acid isobutyl ester is added under argon. After 20 minutes of additional stirring, 2.00 g (8.67 mmol) of benzyloxycarbonylaminoethylamine is added and the batch is allowed to stand overnight. It is suctioned off and the filtrate is evaporated to dryness. The residue is dissolved in methylene chloride, the solution is washed with saturated sodium bicarbonate solution and again evaporated to dryness. The residue is recrystallized from ethyl acetate/hexane. 3.50 g (84% of theory) of 2,3-bis(tert-butoxycarbonylamino)-propionic acid(2-benzyloxycarbonylaminoethyl) amide with a melting point of 152°-154° C. is obtained.

c) 2.02 g of compound obtained under b) is hydrogenated pressureless on the platinum oxide catalyst. After suctioning off, the filtrate is evaporated to oil residue state. 1.51 g (100% of theory) of 2,3-bis(tert-butoxycarbonylamino)propionic acid-(2-aminoethyl) amide is obtained.

| Analysis: | Cld: | C 52.01 | H 8.73 | N 16.17 |
|---|---|---|---|---|
| | Fnd: | C 51.83 | H 8.54 | N 15.91 | d) α) N-{2-[1,2-bis(tert-butoxycarbonylamino)-ethylcarbonylamino]-ethyl}-hematoporphyrin IX 13-amide β) N,N'-bis{2-[1,2-bis(tert-butoxycarbonylamino)-ethyl-carbonylamino]-ethyl}-hematoporphyrin IX 13,17-diamide Under the conditions of example 1, 1.80 g of hematoporphyrin IX, 810 mg (6 mmol) of 1-hydroxybenzotriazole, 2.079 g (6 mmol) of the compound obtained under c) are reacted in the presence of 1.24 g (6 mmol) of dicyclohexylcarbodiimide. The mixture thus obtained is separated by column chromatography on silica gel with isopropanol/methanol (0–100%) into the title compounds. The diamide is eluted as the first compound from the column. Both compounds are obtained as foam.

| α) | Yield: 901 mg (32.4% of theory) | | | | |
|---|---|---|---|---|---|
| | Analysis: | Cld: | C 63.48 | H 7.18 | N 12.09 | O 17.26 |
| | | Fnd: | C 63.51 | H 7.26 | N 12.01 | |
| β) | Yield: 2.103 g (54.6% of theory) | | | | |
| | Analysis: | Cld: | C 59.89 | H 7.38 | N 15.28 | O 17.45 |
| | | Fnd: | C 59.78 | H 7.45 | N 15.22 | | e) N-[2-(1,2-diaminoethylcarbonylamino)-ethyl-hematoporphyrin IX 13-amide

Analogously to example 1c, 927 mg (1 mmol) of the monoamide produced under example d)α) in 15 ml of 2 molar hydrochloric acid in glacial acetic acid is cleaved and worked up.

752.3 mg of the title compound (86.2% of theory) is thus obtained.

| Analysis: | Cld: | C 53.67 | H 6.24 | N 12.84 | Cl 16.25 | O 11.00 |
|---|---|---|---|---|---|---|
| | Fnd: | C 53.56 | H 6.31 | N 12.75 | Cl 15.30 | |

Example 8

N,N'-bis[2-(1,2-diaminoethylcarbonylamino)-ethyl]-hematoporphyrin IX 13,17-diamide Under the conditions of example 1c, 1.284 g (1 mmol) of the diamide produced under example 7d)β) in 20 ml of 2 molar hydrochloric acid in glacial acetic acid is cleaved and worked up.

919.2 mg of the title compound (85.6% of theory) is thus obtained.

| Analysis: | Cld: | C 49.22 | H 6.38 | N 15.65 | Cl 19.81 | O 8.94 |
|---|---|---|---|---|---|---|
| | Fnd: | C 49.28 | H 6.47 | N 15.60 | Cl 19.75 | |

Example 9

N-(13-carboxy-4-oxo-6,9,12-tris(carboxymethyl)-3,6,9,12-tetraazatridecyl)-hematoporphyrin IX 13-amide 1.50 g (2 mmol) of the N-(2-aminoethyl)-hematoporphyrin IX 13-amide trihydrochloride is dissolved in 50 ml of distilled water. A pH of 9 is adjusted by addition of sodium hydroxide solution. 887.4 mg (2.2 mmol) of 3-ethoxycarbonylmethyl-6[2-(2,6-dioxomorpholino)ethyl]-3,6-diazaocatanedioic acid (DTPA monoethyl ester monoanhydride) is added to this solution in portions at 0° C. with stirring, and the pH is kept at 8–9 by sodium hydroxide solution. It is allowed to stand overnight at room temperature at pH 10 and the complexing agent is purified by chromatography on silica gel RP 18. The title compound is eluted by methanol. The combined solutions are evaporated to dryness, the residue is taken up in water and subjected to freeze-drying. The product is obtained as foam.

| Yield: 949.3 mg (84.3% of theory) | | | | | | |
|---|---|---|---|---|---|---|
| Analysis: | Cld: | C 53.33 | H 5.37 | N 11.20 | Na 10.21 | O 19.89 |
| | Fnd: | C 53.21 | H 5.47 | N 11.26 | Na 10.29 | |

Example 10

N-(13-carboxy-4-oxo-6,9,12-tri(carboxymethyl)-3,6,9,12-tetraazatridecyl)3,8-bis(2-hydroxyethyl)-deuteroporphyrin 13-amide Analogously, the corresponding deuteroporphyrin derivative is obtained from the compound obtained in example 4.

| Analysis: | Cld: | C 53.33 | H 5.37 | N 11.20 | Na 10.21 | O 19.89 |
|---|---|---|---|---|---|---|
| | Fnd: | C 53.15 | H 5.42 | N 11.43 | Na 10.52 | |

Example 11

N-(17-carboxy-8-oxo-10,13,16-tris-(carboxymethyl)-7,10,13,16-tetraazaheptadecyl)-hematoporphyrin IX 13-amide Analogously to the conditions of example 9, 806 mg (1 mmol) of the trihydrochloride produced according to example 1c is reacted with 443.7 mg (1.1 mmol) of DPTA monoethyl ester monoanhydride. The title compound is obtained as foam after freeze-drying.

Yield: 1.031 g (87.2% of theory)
Analysis: Cld: C 54.87  H 5.80  N 10.66  Na 9.72  O 18.95
         Fnd: C 54.80  H 5.87  N 10.59  Na 9.67

Example 12

N-{-5,6-bis[9-carboxy-2,5,8-tris-(carboxymethyl)-2,5,8-triazanonylcarbonylamino]-4-oxo-3-azahexyl}-hematoporphyrin IX 13-amide Under the conditions of example 9, 872.7 mg (1 mmol) of diamine, produced according to example 7e in 60 ml of distilled water, is reacted with 887.4 mg (2.2 mmol) of DTPA monoethyl ester monohydride. Working up and purification are also performed as in example 11. The title compound, after freeze-drying, is obtained as foam.

Yield: 1.409 g (84.1% of theory)
Analysis: Cld: C 48.03  H 4.99  N 11.70  Na 12.35  O 22.92
         Fnd: C 48.11  H 5.07  N 11.61  Na 12.41

Example 13

N,N'-bis{-5,6-bis[9-carboxy-2,5,8-tris-(carboxymethyl)-2,5,8-triazanonylcarbonylamino]-4-oxo-3-azahexyl}-hematoporphyrin IX 13,17-diamide Analogously to example 9, 1.074 g (1 mmol) of the tetraamine, produced in example 8, is dissolved in 100 ml of distilled water and reacted with 1.775 g (4.4 mmol) of DTPA-monoethyl ester monohydride. Working up and purification take place also as under example 9. The title compound, after freeze-drying, is obtained as foam.

Yield: 2.101 g (82.7% of theory)
Analysis: Cld: C 47.28  H 5.16  N 13.23  Na 14.48  O 19.86
         Fnd: C 47.21  H 5.24  N 13.29  Na 14.42

Example 14 a) Hematoporphyrin IX manganese(III) acetate, disodium salt 328 mg (4 mmol) of anhydrous sodium acetate, 598.7 mg (1 mmol) of hematoporphyrin IX and 981 mg (4 mmol) of manganese(III) acetate tetrahydrate are dissolved in a mixture of 45 ml of glacial acetic acid and 5 ml of distilled water. It is warmed to 50° C. with stirring, and care is given to exclude light. When no starting material can any longer be detected by thin-layer chromatography, the solution is evaporated to dryness in a vacuum. The residue is suspended with water and made alkaline. It is centrifuged, the solid is separated, washed again with water and the combined solutions are desalted by chromatography on silica gel RP 18 (Merck LiChroprep RP 18). The product is eluted with methanol. The solution is evaporated to dryness in a vacuum, taken up in water and subjected to freeze-drying. The title compound is obtained as foam.

Yield: 659 mg (87.3% of theory)
Analysis: Cld: C      H     N     Mn    Na    O
              57.30  4.94  7.42  7.28  6.09  16.96
         Fnd: C      H     N     Mn    Na
              57.24  5.01  7.36  7.22  6.10

The manganese content is determined with Plasma Quad of the VG company (England).

b) Manganese(III)-[N-(2-tert-butoxycarbonylaminoethyl)-hematoporphyrin IX 13-amide]acetate c) Manganese(III)-[N,N'-bis(2-tert-butoxycarbonylaminoethyl)- hematoporphyrin IX 13,17diamide] acetate 2.264 g (3 mmol) of the manganese complex obtained under a) is dissolved in a mixture of 40 ml of water and 20 ml of dioxane. It is mixed with 3 ml of 1 molar aqueous hydrochloric acid, the solution is evaporated to dryness in a vacuum, dried on the oil pump and the residue is taken up in 300 ml of dimethylformamide. Then it is mixed with 810 mg (6 mmol) of 1-hydroxybenzotriazole [hydrate: 919 mg] and 961.3 mg (6 mmol) of N-tert-butyloxycarbonyl-ethylenediamine. With stirring and covering with argon, it is cooled to −10° C. and mixed with 1.24 g (6 mmol) of dicyclohexylcarbodiimide. It is stirred for one hour at this temperature and then allowed to come to room temperature. The course of the reaction is followed by thin-layer chromatography. After 3 days only small amounts of the starting material can be detected. The solution is now evaporated to dryness in the oil pump vacuum. The residue is dissolved in dichloromethane/ethanol and washed with saturated common salt solution. The organic solution is dried on sodium sulfate and evaporated to dryness in a vacuum. The residue is subjected to column chromatography on silica gel. The title compounds are separated with isopropanol/methanol (0–100%). The respective solutions are combined and evaporated to dryness in a vacuum.

b)
Yield: 264 mg (30.9% of theory)
Analysis: Cld: C 60.56  H 6.26  N 9.85  Mn 6.44  O 16.88
         Fnd: C 60.51  H 6.30  N 9.90  Mn 6.39

The manganese content was determined with Plasma Quad.

c)
Yield: 568 mg (57.1% of theory)
Analysis: Cld: C 60.35  H 6.79  N 11.26  Mn 5.52  O 16.08
         Fnd: C 60.29  H 6.85  N 11.20  Mn 5.47

The manganese content was determined with Plasma Quad.

d) Manganese(III)-[N-(2-aminoethyl)-hematoporphyrin IX 13-amide] acetate 853 mg (1 mmol) of the monoamide obtained according to example 14b is dissolved in 30 ml of trifluoroacetic acid and stirred at room temperature. After about 15 minutes no starting material can any longer be detected. The trifluoroacetic acid is drawn off in a vacuum, the residue is dissolved in distilled water, made alkaline with ammonia, evaporated to dryness in a vacuum, dissolved in water and subjected to freeze-drying. The title compound is obtained as foam.

Yield: 659.4 mg (87.6% of theory)
Analysis: Cld: C 60.63  H 6.03  N 11.16  Mn 7.30  O 14.88
         Fnd: C 60.57  H 6.09  N 11.08  Mn 7.24

The manganese content was determined with the ICP device.

The same compound is obtained by reaction of the compound (monoamine) described in example 3c with manganese(II) acetate analogously to example 14a.

Example 15

Manganese(III)-N-(2-aminoethyl)-3,8-bis(2-hydroxyethyl)-deuteroporphyrin 17 amide acetate The title compound is obtained by reaction of the compound described in example 4 with manganese(II) acetate analogously to example 14a.

Analysis: Cld: C 60.63  H 6.03  N 11.16  Mn 7.30  O 14.88
         Fnd: C 60.78  H 6.01  N 11.41  Mn 7.15

Example 16

Manganese(III)-[N,N'-bis(2-aminoethyl)-hematoporphyrin IX 13,17-diamide]acetate

Analogously to the conditions of example b 14d, 995 mg (1 mmol) of the bisamide prepared in example 14c is cleaved with trifluoroacetic acid. The title compound is obtained as foam after freeze-drying.

Yield: 681 mg (85.7% of theory)
Analysis: Cld: C 60.45  H 6.47  N 14.10  Mn 6.91  O 12.08
         Fnd: C 60.52  H 6.51  N 14.06  Mn 6.87

The manganese content is determined with Plasma Quad.

The same compound is obtained by reaction of the compound described in example 5 with manganese(II) acetate analogously to example 14a.

EXAMPLE 17 a)

Manganese(III)-[N-(6-tert-butoxycarbonylaminohexyl)-hematoporphyrin IX 13-amide] acetate b)

Manganese(III)-[N,N'-bis(6-tert-butoxycarbonylaminohexyl)-hematoporphyrin IX 13,17diamide] acetate Under the conditions of example 14a/b, 2.264 g (3 mmol) of the hematoporphyrin IX manganese complex produced under example 14a in 300 ml of dimethylformamide is reacted with 919 mg (6 mmol) of 1-hydroxybenzotriazole hydrate, 1.52 g (6 mmol) of N-BOC-1,6-diaminehexane hydrochloride, 608 mg (6 mmol) of triethylamine and 1.24 g (6 mmol) of dicyclohexylcarbodiimide. Working up and purification correspond to example 14a/b.

a)
Yield: 278.2 mg (30.6% of theory)
Analysis: Cld: C 62.11  H 6.76  N 9.25  Mn 6.04  O 15.84
         Fnd: C 62.01  H 6.81  N 9.18  Mn 6.00

The manganese content is determined with Plasma Quad.

b) Yield: 632.8 mg (60.2% of theory)
Analysis: Cld:  C      H     N       Mn     O
                61.70  7.19  10.66   5.23   15.22
         Fnd:   C      H     N       Mn
                61.76  7.15  10.59   5.19

The manganese content is determined with Plasma Quad.

c) Manganese(III)-[N-(6-aminohexyl)-hematoporphyrin IX 13-amide] acetate

Under the conditions of example 1c, 909 mg (1 mmol) of the N-BOC derivative produced under example 17a in 25 ml of 2 molar hydrochloric acid in glacial acetic acid is cleaved and converted into the hydrochloride. 738.8 mg of the title compound (87.4% of theory) is obtained.

Analysis: Cld:  C       H     N      Mn     Cl     O
                59.68   6.44  9.94   6.50   4.19   13.25
         Fnd:   C       H     N      Mn     Cl
                59.61   6.51  9.87   6.47   4.23

The same compound is obtained by reaction of the compound described in example 1c with manganese(II) acetate analogously to example 14a.

EXAMPLE 18

Manganese(III)-[N-(17-carboxy-8-oxo-10,13,16-tris-(carboxymethyl)-7,10,13,16-tetraazaheptadecyl)-hematoporphyrin IX 13-amide] acetate Analogously to example 9, 845.3 mg (1 mmol) of the amine hydrochloride produced under example 17c in 50 ml of distilled water is reacted with 443.7 mg (1.1 mmol) of DTPA-monoethyl ester monoanhydride. The title compound is obtained as foam in the form of the pentasodium salt by freeze-drying.

Yield: 1.102 g (85% of theory)
Analysis: Cld:  C      H     N      Na     Mn    O
                52.01  5.38  9.75   8.82   4.25  19.79
         Fnd:   C      H     N      Na     Mn
                51.96  5.44  9.80   8.76   4.22

The same compound is obtained by reaction of the compound obtained in example 9 with manganese(II) acetate analogously to example 14a. If manganese(II) acetate is replaced by gallium(II) chloride, the corresponding gallium complex is obtained.

Example 19

N-(13-carboxy-4-oxo-6,9,12-tris-(carboxylatomethyl)-3,6,9,12-tetraazatridecyl)-hematoporphyrin IX 13-amide, gadolinium complex 1.50 g (2 mmol) of the N-(2-aminoethyl)-hematoporphyrin IX 13-amide trihydrochloride produced according to example 3c is dissolved in 50 ml of distilled water.

A pH of 9 is adjusted by addition of sodium hydroxide solution. 806 mg (2 mmol) of DTPA monoethyl ester monoanhydride is added in portions to this solution at 0° C. with stirring, and the pH is maintained by sodium hydroxide solution. Then it is allowed to stand for four hours at room temperature at a pH of 10, then it is brought to a pH of 7.5 with dilute hydrochloric acid and mixed by portions with 813 mg (2 mmol) of gadolinium acetate tetrahydrate, and also the pH is maintained by addition of sodium hydroxide solution. It is stirred overnight, the solution is evaporated to dryness in a vacuum and the product is purified by chromatography on silica gel RP 18. The solution is concentrated by evaporation, taken up in water and subjected to freeze-drying.

Yield: 1.95 (80.3% of theory)

| Analysis: | | C | H | N | Na | Gd | O |
|---|---|---|---|---|---|---|---|
| Cld: | | 49.46 | 4.98 | 10.38 | 3.79 | 12.95 | 18.45 |
| End: | | C | H | N | Na | Gd | |
| | | 49.38 | 5.05 | 10.29 | 3.69 | 12.90 | |

The gadolinium content is determined by AAS (Atomic Absorption Spectroscopy).

Example 20

N-(13-carboxy-4-oxo-6,9,12-tris-(carboxylatomethyl)-3,6,9,12-tetraazatridecyl-3,8-bis(2-hydroxyethyl)-deuteroporphyrin 13-amide The isomeric compound is obtained, analogously to instruction for example 19, from the trihydrochloride described in example 10.

| Analysis: | C | H | N | Na | Gd | O |
|---|---|---|---|---|---|---|
| Cld: | 49.46 | 4.98 | 10.38 | 3.79 | 12.95 | 18.45 |
| Fnd: | C | H | N | Na | Gd | |
| | 49.71 | 4.82 | 10.53 | 3.59 | 12.86 | |

Analogously, the corresponding dysprosium complex compound is obtained by using dysprosium acetate instead of gadolinium acetate.

| Analysis: | C | H | N | Na | Dy | O |
|---|---|---|---|---|---|---|
| Cld: | 49.24 | 4.96 | 10.34 | 3.77 | 13.32 | 18.37 |
| Fnd: | C | H | N | Na | Dy | |
| | 49.13 | 4.82 | 10.81 | 3.51 | 13.01 | |

Example 21

N-(17-carboxy-8-oxo-10,13,16-tris-(carboxylatomethyl)-7,10,13,16-tetraazaheptadecyl)-hematoporphyrin IX 13-amide, gadolinium complex Analogously to the conditions of example 19, 940 mg (1.2 mmol) of the 13-monoamide trihydrochloride produced according to example 1c, 580 mg (1.44 mmol) of DTPA-monoethyl ester monoanhydride and 674 mg (1.44 mmol) of gadolinium acetate tetrahydrate in 100 ml of distilled water are reacted. Purification takes place by column chromatography on silica gel RP 18, methanol is used as eluant.

| Analysis: | C | H | N | Na | Gd | O |
|---|---|---|---|---|---|---|
| Cld: | 51.05 | 5.40 | 9.92 | 3.62 | 12.38 | 17.63 |
| Fnd: | C | H | N | Na | Gd | |
| | 50.98 | 5.47 | 9.87 | 3.58 | 12.30 | |

The gadolinium determination takes place by AAS.

Example 22

N-{5,6-bis[9-carboxy-2,5,8-tris-(carboxylatomethyl)-2,5,8-triazanonylcarbonylamino]-4-oxo-3-azahexyl}-hematoporphyrin IX 13-amide, digadolinium complex 1.675 g (1 mmol) of the complexing agent produced under example 12 is dissolved in 100 ml of distilled water and the pH is adjusted to 7.5. 812.9 mg (2 mmol) of gadolinium acetate tetrahydrate is added by portions to the desired solution, and the pH is kept constant by addition of sodium hydroxide solution. It is stirred overnight, the complex is purified by column chromatography on silica gel RP, the product-containing eluates are evaporated to dryness in a vacuum, the residue is taken up in water and the title compound is obtained by freeze-drying.

Yield: 1.615 g (87.2% of theory)

| Analysis: | C | H | N | Na | Gd | O |
|---|---|---|---|---|---|---|
| Cld: | 43.45 | 4.52 | 10.59 | 3.72 | 16.98 | 20.73 |
| Fnd: | C | H | N | Na | Gd | |
| | 43.39 | 4.59 | 10.52 | 3.64 | 16.90 | |

The gadolinium content is determined by AAS.

Example 23

N,N'-bis{5,6-bis[9-carboxy-2,5,8-tris-(carboxylatomethyl)-2,5,8-triazanonylcarbonylamino]-4-oxo-3-azahexyl}-hematoporphyrin IX 13,17-diamide, tetragadolinium complex Under the conditions of example 19, 1.2703 g (0.5 mmol) of the complexing agent produced under example 12 is dissolved in 100 ml of distilled water and reacted with 812.9 mg (2 mmol) of gadolinium acetate tetrahydrate. Working up and purification of the complexing agent take place according to example 19. The title compound is obtained as foam.

Yield: 1.185 g (81.9% of theory)

| Analysis: | C | H | N | Na | Gd | O |
|---|---|---|---|---|---|---|
| Cld: | 41.51 | 4.53 | 11.62 | 3.18 | 21.74 | 17.43 |
| Fnd: | C | H | N | Na | Gd | |
| | 41.46 | 4.60 | 11.57 | 3.11 | 21.68 | |

The gadolinium content is determined by AAS.

Example 24 a)

N-[9,10-bis(tert-butoxycarbonylamino)-8-oxo-7-azadecyl-hematoporphyrin IX 13-amide 806 mg (1 mmol) of the amino derivative produced under example 1c is dissolved in a mixture of 50 ml of water and 25 ml of dioxane. The solution is brought to a pH of 8 by sodium hydroxide solution. It is cooled to 4° C. and a solution of 401.4 mg (1 mmol) of 2,3-bis(tert-butoxycarbonylamino)-propionic acid hydroxysuccinimide ester is instilled in it. The reaction is followed by thin-layer chromatography. It is evaporated to dryness in a vacuum, taken up in ethyl acetate and washed with sodium bicarbonate solution, dilute citric acid and common salt solution, the organic solution is dried on sodium sulfate, is concentrated by evaporation in a vacuum and the residue is subjected to column chromatography on silica gel, and isopropyl, to which methanol is added in increasing amounts, is used at eluant. The title compound is obtained as foam.

Yield: 676.5 mg (68.8% of theory)
Analysis: Cld: C 64.74   H 7.59   N 11.40   O 16.27
         Fnd: C 64.68   H 7.66   N 11.43 b)
N-{9,10-bis[9-carboxo-2,5,8-tris-(carboxymethyl)-2,5,8-triazonylcarbonylamino-8-oxo-7-azadecyl}-hematoporphyrin IX 13-amide 983.2 mg (1 mmol) of the monoamide produced under example 24a is dissolved in 20 ml of 2 molar hydrochloric acid in glacial acetic acid and stirred for one hour at room temperature with exclusion of moisture. Then no starting material can any longer be detected in the thin-layer chromatogram. It is evaporated to dryness in a vacuum, the residue is taken up in 50 ml of distilled water, a pH of 9 is adjusted by addition of sodium hydroxide solution, it is cooled to 0° C. and 887.4 mg (2.2 mmol) DTPA-monoethyl ester monoanhydride is added by portions with stirring, and the pH is kept between 8-9 by addition of sodium hydroxide solution. It is stirred for another hour, the solution is adjusted to a pH of 10 and allowed to stand overnight. Then it is neutralized to a pH of 7.5 with hydrochloric acid and mixed by portions with stirring with 894.2 mg (2.2 mmol) of gadolinium acetate, and the pH is also maintained by addition of sodium hydroxide solution. It is allowed to stir for another 4 hours, the solution is concentrated by evaporation in a vacuum and the product is purified by column chromatography on silica gel RP 18. The title compound is obtained by freeze-drying.

Yield: 1.322 g (69.3% of theory)
Analysis: Cld: C      H     N      Na    Gd     N
               44.69  4.81  10.28  3.61  16.48  20.12
         Fnd: C      H     N      Na    Gd     N
               44.60  4.86  10.20  3.55  16.39  20.16

The gadolinium content is determined by AAS.

Example 25
N,N'-(17-carboxy-8-oxo-10,13,16-tris-(carboxylatomethyl)-7,10,13,16-tetraazaheptadecyl)-hematoporphyrin IX 13,17-diamide, digadolinium complex Analogously to the conditions of example 19, 615 mg (0.65 mmol) of the 3,17-diamide of example 2, 807 mg (2.0 mmol) of DTPA-monoethyl ester monoanhydride and 937 mg (2.0 mmol) of gadolinium acetate tetrahydrate in 100 ml of distilled water are reacted. Purification takes place by column chromatography on silica gel RP, methanol is used as eluant.

Yield: 1.49 (78.4% of theory)
Analysis: Cld: C      H     N      Na    Gd     O
               46.83  5.31  10.33  2.42  16.57  18.54
         Fnd: C      H     N      Na    Gd
               46.75  5.40  10.28  2.39  16.43

The gadolinium content was determined by AAS.

Example 26
N,N'-bis(13-carboxy-4-oxo-6,9,12-tris-(carboxylatomethyl)-3,6,9,12-tetraazatridecyl)-hematoporphyrin IX 13,17-diamide, digadolinium complex Analogously to example 25, 413.4 mg (0.5 mmol) of the diamide of example 5, 807 mg (2.0 mmol) of DTPA-monoethyl ester monoanhydride and 937 mg (2.0 mmol) of gadolinium acetate tetrahydrate in 100 ml of distilled water are reacted. Purification takes place by column chromatography on silica gel RP. The title compound is obtained by freeze-drying of the aqueous solution.

Yield: 707 mg (81.8% of theory)
Analysis: Cld: C      H     N     Na    Gd     O
               44.49  4.55  9.73  2.66  18.20  20.37
         Fnd: C      H     N     Na    Gd
               44.41  4.60  9.68  2.62  18.15

The gadolinium content was determined by AAS.

Example 27
Manganese(III)-[N-(17-carboxy-8-oxo-10,13,16-tris-(carboxylatomethyl)-7,10,13,16-tetraazaheptadecyl)-hematoporphyrin IX 13-amide]acetate, gadolinium complex 909 mg (1 mmol) of the protected monoamide produced under example 17a is cleaved with hydrochloric acid in glacial acetic acid as under example 17c and then in distilled water is reacted with 443.7 mg (1.1 mmol) of DTPA-monoethyl ester monoamide to the complexing agent and then reacted with 447.1 mg gadolinium acetate tetrahydrate according to the instruction for example 19 to the title compound. After freeze-drying of the purified substance, 935.9 mg (67.7% of theory) is obtained as foam.

Analysis: Cld: C      H     N     Na    Gd     Mn    O
               48.66  5.03  9.12  3.33  11.38  3.97  18.52
         Fnd: C      H     N     Na    Gd     Mn
               48.59  5.10  9.14  3.36  11.30  3.94

The metal content is determined with Plasma Quad.

Example 28
Manganese(III)-[N-(13-carboxy-4-oxo-6,9,12-tris-(carboxylatomethyl)-3,6,9,12-tetraazatridecyl)-hematoporphyrin IX 13-amide] acetate, gadolinium complex 853 mg (1 mmol) of the protected monoamide of the hematoporphyrin manganese complex produced under example 14b is dissolved in 30 ml of trifluoroacetic acid and stirred at room temperature. After about 15 minutes no starting material is detectable by thin-layer chromatography. It is evaporated to dryness in a vacuum, taken up in 100 ml of distilled water, cooled to 0° C., adjusted to a pH of 9 by addition of sodium hydroxide solution and 443.4 mg (1.1 mmol) of DTPA-monoethyl ester monoanhydride is added in portions with stirring, and the pH is maintained by addition of sodium hydroxide solution. It is stirred for two more hours, then a pH of 10 is adjusted and it is allowed to stand overnight. Then it is neutralized to a pH of 7.5 with dilute hydrochloric acid and mixed by portions with 447.1 mg (1.1 mmol) of gadolinium acetate tetrahydrate, and the pH is also maintained by addition of sodium hydroxide solution. It is allowed to stir overnight and the product is purified by chromatography on silica gel RP. The product-containing solution is evaporated to dryness in a vacuum, taken up in water and freeze-dried. The title compound is obtained as foam.

Yield: 1.089 g (82.1% of theory)

| Analysis: | | C | H | N | Na | Mn | Gd | O |
|---|---|---|---|---|---|---|---|---|
| | Cld: | 47.09 | 4.64 | 9.50 | 3.47 | 4.14 | 11.86 | 19.30 |
| | Fnd: | C | H | N | Na | Mn | Gd | |
| | | 47.02 | 4.70 | 9.45 | 3.50 | 4.10 | 11.78 | |

The metal content is determined with Plasma Quad.

The compound is also obtained in the following way: 123 mg (1.5 mmol) of anhydrous sodium acetate is added to a mixture of 22 ml of glacial acetic acid and 2 ml of distilled water and is warmed to 50° C. Then 380 mg (0.32 mmol) of the gadolinium complex produced under example 19 as well as 368 mg (1.5 mmol) of magnesium(II) acetate tetrahydrate are added and stirred for about 2 hours at this temperature with exclusion of light. No starting material can any longer be detected in the thin-layer chromatogram. It is evaporated to dryness in a vacuum, it is taken up in water, filtered and purified by chromatography on silica gel RP. The product-containing solutions are combined, evaporated to dryness in a vacuum, taken up in water and subjected to freeze-drying. Thus, 357.8 mg (84.3% of theory) of the title compound is obtained.

Manganese and gadolinium are determined with Plasma Quad.

| Analysis: | | C | H | N | Na | Mn | Gd | O |
|---|---|---|---|---|---|---|---|---|
| | Cld: | 47.09 | 4.64 | 9.50 | 3.47 | 4.14 | 11.86 | 19.30 |
| | Fnd: | C | H | N | Na | Mn | Gd | |
| | | 47.02 | 4.71 | 9.46 | 3.43 | 4.09 | 11.80 | |

EXAMPLE 29

Manganese(III)-[N,N'-bis(13-carboxy-4-oxo-6,9,12-tris-(carboxylatomethyl)-3,6,9,12-tetraazatridecyl)hematoporphyrin IX 13,17-diamide) acetate, digadolinium complex The substance of example 16 obtained from 995 mg (1.0 mmol) of the starting material after cleavage of the nitrogen protecting groups is reacted in 100 ml of distilled water with 887.4 mg (2.2 mmol) of the DTPA-monoethyl ester monoanhydride as well as 894 mg (2.2 mmol) of gadolinium acetate tetrahydrate analogously to example 19 and purified. The title compound is obtained as foam.

Yield: 1.562 g (82.3% of theory)

| Analysis: | | C | H | N | Na | Mn | Gd | O |
|---|---|---|---|---|---|---|---|---|
| | Cld: | 43.03 | 4.51 | 10.33 | 2.42 | 2.89 | 16.57 | 20.23 |
| | Fnd: | C | H | N | Na | Mn | Gd | |
| | | 42.97 | 4.57 | 10.28 | 2.38 | 2.86 | 16.49 | |

The metal determination is performed with Plasma Quad.

The same compound is also obtained as follows:

Analogously to example 14a, 1037 mg (0.6 mmol) of the digadolinium complex produced under example 26 is added to the solution of 197 mg (2.4 mmol) of anhydrous sodium acetate with a temperature of 50° C. in a mixture of 45 ml of glacial acetic acid and 5 ml of distilled water. Then 588 mg (2.4 mmol) of manganese(II) acetate tetrahydrate is added thereto and stirred, with exclusion of light, until no starting material can be detected in the thin-layer chromatogram. After working up, 906.5 mg (79.6% of theory) of the title compound is obtained.

Manganese and gadolinium are determined with Plasma Quad.

| Analysis: | | C | H | N | Na | Mn | Gd | O |
|---|---|---|---|---|---|---|---|---|
| | Cld: | 43.03 | 4.51 | 10.33 | 2.42 | 2.89 | 16.57 | 20.23 |
| | Fnd: | C | H | N | Na | Mn | Gd | |
| | | 42.98 | 4.60 | 10.28 | 2.37 | 2.87 | 16.52 | |

EXAMPLE 30

3,8-bis[1-(13-carboxy-4-oxo-6,9,12-tris-(carboxymethyl)-3,6,9,12-tetraazatridecylthio)-ethyl]-deuteroporphyrin, digadolinium complex a) 1.0 g (1.5 mmol) of hematoporphyrin IX dihydrochloride and 1.9 g (16.6 mmol) of mercaptoethylamine hydrochloride are reacted under argon for 40 minutes at room temperature with 10 ml of a 33% solution of hydrogen bromide in glacial acetic acid. After evaporation to dryness, the residue is dissolved under argon in 50 ml of 1N sodium hydroxide solution, neutralized with 5N hydrochloric acid and the solution is chromatographed on an RP 18 silica gel column (Merck). By elution with a 20% solution of ammonia in methanol, after concentration by evaporation, 500 mg (38.6% of theory) of 3,8-bis[1-(2-aminoethylthio)-ethyl]-deuteroporphyrin-tetrahydrochloride is obtained.

| Analysis: | Cld: | C 52.90 | H 6.07 | N 9.74 | S 7.43 | Cl 16.43 |
|---|---|---|---|---|---|---|
| | Fnd: | C 53.55 | H 6.83 | N 9.51 | S 7.24 | Cl 16.66 | b) 500 mg 10.65 mmol) of the compound obtained under a) is suspended in 100 ml of dilute sodium hydroxide solution (pH 9) and mixed at 50° C. with 726 mg of DTPA-monoethyl ester monoanhydride (1.8 mmol) (pH 7.5). It is brought to pH 10 by addition of 1N sodium hydroxide solution and stirred for two days at room temperature. The solution is then brought to pH 7.5 with N hydrochloric acid and mixed with 862 mg gadolinium(III) acetate tetrahydrate (1.8 mmol). After stirring for three days at room temperature, the resulting precipitate is suctioned off and dissolved in mixture of ethanol/1N hydrochloric acid. The solution is chromatographed on an RP 18 silica gel column (Merck). By elution with a 20% solution of ammonia in methanol, after concentration by evaporation, 350 mg (58% of theory) of the tetrasodium salt of the title compound is obtained.

| Analysis: | Cld: | C 43.03 | H 4.43 | N 9.13 | Gd 17.07 | S 3.48 |
|---|---|---|---|---|---|---|
| | Fnd: | C 43.14 | H 4.61 | N 9.34 | Gd 17.21 | S 3.30 |

EXAMPLE 31

3,8-bis[1-(10-carboxy-1-oxo-3,6,9,-tris-(carboxymethyl)-3,6,9-triazadecylamino)-ethyl]-deuteroporphyrin, digadolinium complex Analogously to the instruction for example 30, the tetrasodium salt of the title compound is obtained from 3,8-bis(1-bromoethyl)-deuteroporphyrin dihydrobromide by reaction with the potassium salt of bis(tert-butoxycarbonyl)imide, cleavage of the protecting groups and reaction with DTPA-monoethyl ester monohydride and complexing with gadolinium(III) acetate tetrahydrate.

| Analysis: | Cld: | C 43.30 | H 4.57 | N 10.71 | Gd 17.10 |
|---|---|---|---|---|---|
| | Fnd: | C 43.15 | H 4.77 | N 10.52 | Gd 17.41 |

EXAMPLE 32

Dimanganese(III) N,N'-[4,14-dioxo-6,9,12-tris-(carboxylatomethyl)-3,6,9,12,15-pentaaza-1,17-heptadecylmethylene]-bis(hematoporphyrin)-IX-13-amide diacetate, pentasodium salt 1.21 g (1.61 mmol) of manganese(III)-[N-(2-aminoethyl)- hematoporphyrin IX 13-amide] acetate (example 14d)is dissolved in 35 ml of water by addition of n sodium hydroxide solution at pH 10. The solution is mixed at 0° C. by portions with 0.29 g (0.805 mmol) of 1.5-bis(2,6-dioxomorpholino)-3-azapentane-3-acetic acid, and the pH is maintained at 9.5 to 10 by instilling of n sodium hydroxide solution. It is stirred for three more hours at room temperature and the solution is evaporated to dryness. The residue is dissolved in 100 ml of glacial acetic acid and, after addition of 394 mg (1.61 mmol) of manganese(II) acetate tetrahydrate the solution is heated to 50° C. for three hours. The solution is evaporated to dryness, the residue is taken up in water and the solution is chromatographed on silica gel. After freeze-drying, 1.56 g (79% of theory) of the title compound is obtained as white powder.

| Analysis: | Cld: | C 54.80 | H 5.31 | N 10.65 | Mn 5.57 |
|---|---|---|---|---|---|
| | Fnd: | C 54.63 | H 5.52 | N 10.33 | Mn 5.40 (anhydrous substance) |

EXAMPLE 33

Production of a contrast agent for nuclear medical use with $^{111}$In 2.252 mg (2 micromol) of the compound described in example 9 is dissolved in 3 ml of sterile, pyrogen-free 0.1M citrate buffer (ph 5.8). The solution is filtered over a Millipore Filter (0.2 microns) into a Multivial and mixed with 0.1 ml of a physiological salt solution containing 1.3 mCi $^{111}$In Cl$_3$. The solution is ready to use.

Analogously, the corresponding $^{111}$In radiodiagnostic agent is obtained from the gallium complex mentioned in example 18.

EXAMPLE 34

Production of a contrast agent for nuclear medical use with $^{99m}$Tc 1.689 mg (1.5 micromol) of the compound described in example 9 is dissolved in 1.5 ml of sterile, distilled water and mixed with 0.26 mg of sodium hydrogen sulfite (1.5 micromol). After addition of 0.1N hydrochloric acid to pH 5.8, the solution is poured over a Millipore Filter (0.2 micron) and put into a Multivial under nitrogen gassing. After addition of 0.5 ml of a physiological salt solution, which contains 5.0 mCi of technetium ($^{99m}$Tc) pertechnetate, a solution ready to use is obtained.

EXAMPLE 35

Production of a contrast agent for NMR diagnosis 46.4 g (35 mmol) of the compound described in example 28 is dissolved neutral in 500 ml of a sterile and pyrogen-free buffer solution (0.1M sodium bicarbonate) with addition of 500 mg of the calcium trisodium salt of diethylenetriaminepentaacetic acid and with the introduction of carbon dioxide. The solution is filtered sterile and put into bottles in 50-ml portions.

EXAMPLE 36

Production of a contrast agent for NMR diagnosis 45.29 g (35 mmol) of the compound described in example 18 is dissolved neutral in 500 ml of a sterile and pyrogen-free buffer solution (0.1M sodium bicarbonate) with addition of 500 mg of the calcium disodium salt of diethylenetriaminepentaacetic acid and by gassing with carbon dioxide. The sterile-filtered solution is put into Multivials in 50-ml portions.

EXAMPLE 37

Production of a contrast agent for NMR diagnosis 42.49 g (35 mmol) of the compound described in example 19 is dissolved neutral in 500 ml of a sterile and pyrogen-free buffer solution (0.1M sodium bicarbonate) with addition of 500 mg of the calcium trisodium salt of diethylenetriaminepentaacetic acid and by gassing with carbon dioxide. The sterile-filtered solution is put into bottles in 50-ml portions.

EXAMPLE 38

Production of a contrast agent for NMR diagnosis 691.2 g (0.4 mol) of the compound described in example 26 is dissolved neutral with warming in 500 ml of a sterile and pyrogen-free buffer solution (0.1M sodium bicarbonate) with addition of 500 mg of the calcium disodium salt of diethylenetriaminepentaacetic acid and by gassing with carbon dioxide. The sterile-filtered solution is put into bottles in 50-ml portions.

EXAMPLE 39 a) 3,6-bis(1-methoxyethyl)-deuteroporphyrin 13,17-dihydrazide 1.0 g (1.53 mmol) of hematoporphyrin IX dimethyl ester dimethyl ether is dissolved in 20 ml of pyridine (S. Kojo and S. Sano, J. Chem. Soc. Perkin I, 2864, 1981), mixed with 6 ml of hydrazine hydrate (80%) and stirred overnight at room temperature. No starting material can be detected in the thin-layer chromatogram. The solution is evaporated to dryness in a vacuum. The title compound is purified by column chromatography on silica gel with ethanol as eluant. After drying in a vacuum, the product is obtained as foam.

| Yield: 0.73 g (72.9% of theory) | | | | |
|---|---|---|---|---|
| Analysis: | Cld: | C 66.03 | H 7.08 | N 17.11 |
| | Fnd: | C 66.24 | H 6.95 | N 16.95 | b)

N,N'-bis[10-ethoxycarbonyl-3,6,9-tris-(carboxylatomethyl)-3,6,9-triazadecanoylamino]-3,8-bis(1-methoxyethyl)-deuteroporphyrin 13,17-diamide, gadolinium complex 654.8 g (1 mmol) of the dihydrazide produced according to example 39a) is dissolved in a mixture of 60 ml of dioxane and 40 ml of distilled water. It is then reacted at 0° C. with stirring with 1.211 g (3.0 mmol) of 3-ethoxycarbonylmethyl-6-[2-(2,6-dioxomorpholino)ethyl]-3,6-diazooctanedioic acid, and the pH of the solution is kept between 8–9 by addition of sodium hydroxide solution. The solution is stirred for 2 more hours. Then the pH of the solution is adjusted to 7.5 with dilute hydrochloric acid and then 1.219 g (3 mmol) of gadolinium acetate tetrahydrate is added by portions, and the pH is again maintained by addition of sodium hydroxide solution. After stirring overnight, it is evaporated to dryness in a vacuum. The product is purified by chromatography on silica gel RP 18. The solution containing the title compound is evaporated to dryness in a vacuum, taken up in distilled water and subjected to freeze-drying.

Yield: 1.347 g (76.1% of theory)
Analysis: Cld: C 46.14  H 5.13  N 11.08  Gd 17.77  O 19.89
         Fnd: C 46.02  H 5.24  N 11.17  Gd 17.61

EXAMPLE 40

NMR Diagnosis In Vivo

The gadolinium complex of the manganese(III)-[N-(13-carboxy-4-oxo-6,9,12-tris-(carboxylatomethyl)-3,6,9,12-tetraazatridecyl)- hematoporphyrin IX 13-amide] acetate, disodium salt (example 28) was applied i.v. in a dosage of 0.1 mmol/kg of a naked mouse (Babl/c. nu/nu,=20 g) with a subcutaneous HT29 colon tumor. After dissolution of the substance it was adjusted to a pH of 7.5. The examination was performed in a nuclear magnetic tomograph (General Electric Company) with a 2-tesla magnet.

Photographs were taken before and after application of the contrast agent ($T_R=400$ msec. $T_E=30$ msec) in the area of the liver and of the tumor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A porphyrin complex compound, comprising at least one porphyrin ligand of formula I

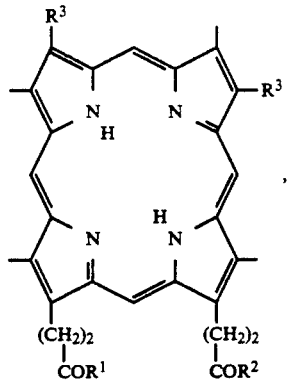

wherein
$R^1$ and $R^2$ are, each independent of one another, OH or a $(NH)_x$—[—$Q(NH)_y$]$_w$—W group,
wherein
x and y each independently is 0, 1 or 2;
w is 0 or 1;
Q is $C_0$–$C_{20}$ alkylene;
W is H or the group V-K, wherein
V is a straight-chain, branched, saturated or unsaturated $C_0$–$C_{20}$-hydrocarbylene, optionally substituted by hydroxy, oxo, and/or NHK group(s), optionally containing imino, polyethylenoxy, phenylenoxy, phenylenimino, amido, hydrazido, ester group(s), oxygen, sulfur and/or nitrogen atom(s);
K is H or a complexing agent of formula IA, IB, IC or ID, $$\underset{CH_2CO_2H}{\overset{CH_2Z}{N}}-CH_2-CH_2-\underset{R^4}{\overset{CH_2CO_2H}{N}}_{\overline{n}}CH-CH_2-\underset{}{\overset{CH_2CO_2H}{N}}-CH_2-CH_2)_{\overline{m}}\underset{CH_2CO_2H}{\overset{CH_2X}{N}} \quad (IA)$$

$$\underset{CH_2CO_2H}{\overset{CH_2Z}{N}}-CH_2-CH_2-\overline{N})_{\overline{n}}CH_2-\underset{R^4}{CH}-\underset{}{N}-CH_2-CH_2)_{\overline{m}}\underset{CH_2CO_2H}{\overset{CH_2X}{N}} \quad (IB)$$

(IC)
$$\begin{array}{c} (CH_2)_sZ \quad R^4 \quad CH_2X \\ | \quad\quad | \quad\quad | \\ N(CH_2)_{\overline{k}}CH(CH_2)_{\overline{l}}N \\ | \quad\quad\quad\quad | \\ B \quad\quad\quad D \\ | \quad\quad\quad\quad | \\ N\text{———}(E-N)_q \\ | \quad\quad\quad\quad | \\ CH_2CO_2H \quad CH_2CO_2H \end{array}$$

(ID)
$$\begin{array}{c} CH_2Z \quad\quad CH_2X \\ | \quad\quad\quad | \\ N-CHR^5-CHR^6-N \\ | \quad\quad\quad\quad | \\ CH_2CO_2H \quad CH_2CO_2H \end{array}$$

provided that either Z or $R^4$ is bonded to V, and wherein
n and m each independently is 0, 1, 2, 3 or 4, and n and m add to no more than 4,
k is 1, 2, 3, 4 or 5,
l is 0, 1, 2, 3, 4 or 5
q is 0, 1 or 2,
s is 0 or 1, B, D and E, which are the same or different, each are $$-(CH_2)_u-(CH)_v-(CH_2)_r-,$$
$$\phantom{-(CH_2)_u-(}{}^{|}R^7$$

wherein $R^7$ is H or a straight-chain, branched, saturated or unsaturated $C_1-C_{20}$-hydrocarbyl, optionally substituted by hydroxy and/or amino group(s), optionally containing oxygen and/or nitrogen atom(s);

u is 0, 1, 2, 3, 4 or 5;

v is 0 or 1;

and

B, D and E each contain, aside from group $R^7$, at least 2 and at most 5 carbon atoms;

Z is $$-CO_2H \text{ or } -\overset{O}{\underset{\|}{C}}-;$$

X is $$-CO_2H \text{ or } -\overset{O}{\underset{\|}{C}}-I''$$

wherein $I''$ is independently another ligand of formula I, and the radical W contained in $R^1$ and $R^2$ is a direct bond;

$R^4$ is a direct bond or H;

$R^5$ and $R^6$ together are a dimethylene- or trimethylene-methine group optionally substituted by 1-2 hydroxy or 1-3 $C_1-C_4$ alkyl groups, (when Z is $-CO_2H$), or together are a trimethylene or tetramethylene group optionally substituted by 1-2 hydroxy or 1-3 $C_1-C_4$ alkyl groups when Z is $$-\overset{O}{\underset{\|}{C}}-,$$

provided that x and w are not simultaneously 0 when V is a $C_0$ alkylene chain; and that Z is $$-\overset{O}{\underset{\|}{C}}-$$

$R^4$ is H, and that Z is $-CO_2H$ when $R^4$ is a direct bond and s is 1; each $R^3$ is independently $-CH(OH)CH_3$ or $-CH_2CH_2OH$, provided that $R^1$ and $R^2$ are not simultaneously OH, and that optionally a portion of the $CO_2H$ groups can be present as ester and/or amide groups;

and further optionally the hydroxy group in each $R^3$ group can independently be present as $C_{1-4}$-ester;

and containing at least one ion of an element of atomic numbers 21-29, 42, 44 or 57-83 which is chelated by a complexing agent of group K, the porphyrin skeleton, or both, with the proviso that the porphyrin skeleton does not chelate a metal ion other than manganese, and optionally comprising cations of inorganic and/or organic bases, amino acids or amino acid amides.

2. A compound of claim 1, wherein said compound contains at least one paramagnetic ion of an element of atomic numbers 21-29, 42, 44 or 57-70.

3. A compound of claim 1, wherein the porphyrin skeleton contains no metal ion.

4. A compound of claim 1, wherein V is
$-(CH_2)_2NH-$; $-CH_2-O-C_6H_4-CH_2-$; $-CH_2-CH(OH)-O-C_6H_4-CH_2-$;
$-(CH_2)_4-NH-CO-CH_2-O-C_6H_4-CH_2-$;
$-(CH_2)_4-NH-CH_2-CH(OH)-CH_2-O-C_6H_4-CH_2-$; $-(CH_2)_3-O-C_6H_4-CH_2$;
$-CH_2-CO-NH-(CH_2)_3-O-CH_2-$; $-CH_2-CO-NH-NH-$; $-CH_2-CO-NH-(CH_2)_2-$;
$-CH_2-CO-NH(CH_2)_{10}-$; $-CH_2-CO-NH-(CH_2)_2-S-$; $-(CH_2)_4-NH-CO-(CH_2)_8-$;
$-CH_2-CO-NH-(CH_2)_3-NH$; $-(CH_2)_3-NH-$;
$-CO-CH(NHK)-CH_2NHK-$; $-CH(CH_3)-S-(CH_2)_2-NH-$; or
$-(CH_2)_2NH-CO-CH_2-(OCH_2CH_2)_{43}-OCH_2$.

5. A compound of claim 1, wherein the porphyrin skeleton chelates manganese.

6. A compound according to claim 5, wherein at least one of $R^1$ and $R^2$ is $(NH)_x-[Q-(NH)_y]_w-V-K$ and K is a complexing agent of formula IA, IB, IC or ID and said complexing agent contains at least one paramagnetic metal ion of an element of atomic numbers 21-29, 42, 44 or 57-70.

7. A compound according to claim 1, wherein at least one of $R^1$ and $R^2$ is $(NH)_x-[Q-(NH)_y]_w-V-K$ and K is ethylenediaminetetraacetic acid, diethylenetriaminepentaacetic acid, trans-1,2-cyclohexanediaminetetraacetic acid, 1,4,7,10-tetraazacyclododecanetetraacetic acid, 1,4,7-triazacyclononanetriacetic acid, 1,4,8,11-tetraazatetradecanetetraacetic acid or 1,5,9-triazacyclododecanetriacetic acid, bonded to the porphyrin skeleton via a carbon atom or a carbonyl group.

8. A compound according to claim 1, wherein both $R^3$ groups are $-CHOHCH_3$.

9. A compound according to claim 1, wherein both $R^3$ groups are $-CH_2CH_2OH$.

10. A compound according to claim 1, wherein $R^1$ is OH and $R^2$ is $(NH)_x-[Q-(NH)_y]_w-W$.

11. A compound according to claim 1, wherein $R^1$ and $R^2$ are each a $(NH)_x-[Q-(NH)_y]_w-W$ group.

12. A compound according to claim 1, wherein said compound is (a) manganese(III)-[N-(2-tert-butoxycarbonylaminoethyl)-hematorphyrin IX 13-amide] acetate;

(b) manganese(III)-N,N'-bis(2-tert-butoxycarbonylaminoethyl)-hematoporphyrin IX 13,17-diamide] acetate;

(c) manganese(III)-[N-(2-aminoethyl)-hematoporphyrin IX 13-amide] acetate;

(d) manganese(III)-[N-(2-aminoethyl)-3,8-bis(2-hydroxyethyl)-deuteroporphyrin 17-amide] acetate;

(e) manganese(III)-[N,N'-bis(2-aminoethyl)-hematoporphyrin IX 13,17-diamide] acetate;

(f) manganese(III)-[N-(6-tert-butoxycarbonylaminohexyl)-hematoporphin IX 13-amide] acetate;

(g) manganese(III)-[N,N'-bis(6-tert-butoxycarbonylaminohexyl)-hematoporphyrin IX 13,17-diamide] acetate;

(h) manganese(III)-[N-(6-aminohexyl)-hematoporphyrin IX 13-amide] acetate;

(i) manganese(III)-[N-(17-carboxy-8-oxo-10,13,16-tris(carboxymethyl)-7,10,13,16-tetraazaheptadecyl)-hematoporphyrin IX 13-amide] acetate;

(j) manganese(III)-[N-(17-carboxy-8-oxo-10,13,16-tris(carboxylatomethyl)-7,10,13,16-tetraazaheptadecyl)-hematoporphyrin IX 13-amide] acetate, gadolinium complex; or (k) manganese(III)-[N,N'-bis(13carboxy-4-oxo-6,9,12-tris(carboxylatomethyl)-3,6,9,12-tetraazatridecyl)- hematoporphyrin IX 13,17-diamide] acetate, digadolinium complex.

13. A gadolinium complex of manganese(III)-[N-(13-carboxy-4oxo-6,9,12-tris-(carboxylatomethyl)-3,6,9,12-tetraazatridecyl)-hematoporphyrin IX 13-amide] acetate, a compound of claim 1.

14. A compound of claim 1, which is N-(13-carboxy-4-oxo-6,9,12-tris-(carboxylatomethyl)-3,6,9,12-tetraazatridecyl)-hematoporphyrin IX 13-amide, gadolinium complex.

15. A compound of claim 1, which is manganese(III)-[N-(13-carboxy-4-oxo-6,9,12-tris(carboxylatomethyl)-3,6,9,12-tetraazatridecyl)-hematoporphyrin IX 13-amide)] acetate, gadolinium complex.

16. A pharmaceutical composition comprising at least one compound of claim 1 and a pharmaceutically acceptable carrier.

17. A pharmaceutical composition comprising at least one compound of claim 15, and a pharmaceutically acceptable carrier.

18. A pharmaceutical composition comprising at least one compound of claim 3, and a pharmaceutically acceptable carrier.

19. A pharmaceutical composition comprising at least one compound of claim 4, and a pharmaceutically acceptable carrier.

20. In a method of conducting magnetic resonance imaging wherein a subject is subjected to said imaging, the improvement comprising administering to said subject a compound of claim 2.

21. A method of claim 20, wherein V is —(CH$_2$)$_2$NH—; —CH$_2$—O—C$_6$H$_4$—CH$_2$—; —CH$_2$—CH(OH)—CH$_2$—O—C$_6$H$_4$—CH$_2$—; —(=N-H)—O—C$_6$H$_4$—CH$_2$—; —(CH$_2$)$_4$—NH—CO—CH$_2$—O—C$_6$H$_4$—CH$_2$—; —(CH$_2$)$_4$—NH—CH$_2$—CH(OH)—CH$_2$—O—C$_6$H$_4$—CH$_2$—; —(CH$_2$)$_3$—O—C$_6$H$_4$—CH$_2$; —CH$_2$—CO—NH—(CH$_2$)$_3$—O—CH$_2$—; —CH$_2$—CO—NH—NH—; —CH$_2$—CO—NH—(CH$_2$)$_2$—; —CH$_2$—CO—NH(CH$_2$)$_{10}$—; —CH$_2$—CO—NH—(CH$_2$)$_2$—S—; —(CH$_2$)$_4$—NH—CO—(CH$_2$)$_8$—; —CH$_2$—CO—NH—(CH$_2$)$_3$—NH; —(CH$_2$)$_3$—NH—; —(CH$_2$)NH—C(=S)—NH—C$_6$H$_4$—CH$_2$—; —CO—CH(NHK)—CH$_2$NHK—; —CH(CH$_3$)—S—(CH$_2$)$_2$—NH—; or —(CH$_2$)$_2$NH—CO—CH$_2$—(OCH$_2$CH$_2$)$_{43}$—OCH$_2$.

22. A method of claim 20, wherein the porphyrin skeleton chelates manganese.

23. A method of claim 20, which is a gadolinium complex of N-(13-carboxy-4-oxo-6,9,12-tris-(carboxylatomethyl)-3,6,9,12-tetraazatridecyl)-hematoporphyrin IX 13-amide.

24. A method of claim 20, wherein said compound is manganese(III)-[N-13-carboxy-4-oxo-6,9,12-tris-(carboxylatomethyl)-3,6,9,12-tetraazatridecyl)-hematoporphyrin IX 13-amide] acetate, gadolinium complex.

25. A method of claim 20, wherein at least one of R$^1$ and R$^2$ is (NH)$_x$—[Q—(NH)$_y$]$_w$—V—K and K is a complexing agent of formula IA, IB, IC or ID and said complexing agent contains at least one paramagnetic metal ion of an element of atomic numbers 21-29, 42, 44 or 57-70.

26. A method of claim 20, wherein at least one of R$^1$ and R$^2$ is (NH)$_x$—[Q—(NH)$_y$]$_w$—V—K and K is ethylenediaminetetraacetic acid, diethylenetriamine pentaacetic acid, trans-1,2-cyclohexanediaminetetraacetic acid, 1,4,7,10-tetraazacyclododecanetetraacetic acid, 1,4,7-triazacyclononanetriacetic acid, 1,4,8,11-tetraazatetradecanetetraacetic acid or 1,5,9-triazacyclododecanetriacetic acid, bonded to the porphyrin skeleton via a carbon atom or a carbonyl group.

27. A method of claim 20, wherein both R$^3$ groups are —CHOHCH$_3$.

28. A method of claim 20, wherein both R$^3$ groups are —CH$_2$CH$_2$OH.

29. A method of claim 20, wherein R$^1$ is OH and R$^2$ is (NH)$_x$—[Q—(NH)$_y$]$_w$—W.

30. A method of claim 20, wherein R$^1$ and R$^2$ are each a (NH)$_x$—[Q—(NH)$_y$]$_w$—W group.

31. A method of claim 20, wherein said compound is
(a) manganese(III)-[N-(2-tert-butoxycarbonylaminoethyl)-hematorphyrin IX 13-amide] acetate;

(b) manganese(III)-N,N'-bis(2-tert-butoxycarbonylaminoethyl)-hematoporphyrin IX 13,17-diamide] acetate;

(c) manganese(III)-[N-(2-aminoethyl)-hematoporphyrin IX 13-amide] acetate;

(d) manganese(III)-[N-(2-aminoethyl)-3,8-bis(2-hydroxyethyl)-deuteroporphyrin 17-amide] acetate;

(e) manganese(III)-[N,N'-bis(2-aminoethyl)-hematoporphyrin IX 13,17-diamide] acetate;

(f) manganese(III)-[N-(6-tert-butoxycarbonylaminohexyl)-hematoporphyrin IX 13-amide] acetate;

(g) manganese(III)-[N,N'-bis(6-tert-butoxycarbonylaminohexyl)-hematoporphyrin IX 13,17-diamide] acetate;

(h) manganese(III)-[N-(6-aminohexyl)-hematoporphyrin IX 13-amide] acetate;

(i) manganese(III)-[N-(17-carboxy-8-oxo-10,13,16-tris(carboxymethyl)-7,10,13,16-tetraazaheptadecyl)-hematoporphyrin IX 13-amide] acetate;

(j) manganese(III)-[N-(17-carboxy-8-oxo-10,13,16-tris(carboxylatomethyl)-7,10,13,16-tetraazaheptadecyl)-hematoporphyrin IX 13-amide] acetate, gadolinium complex; or (k) manganese(III)-[N,N'-bis(13carboxy-4-oxo-6,9,12-tris(carboxylatomethyl)-3,6,9,12-tetraazatridecyl)- hematoporphyrin IX 13,17-diamide] acetate, digadolinium complex.

32. A method of claim 20, wherein said compound is administered in an amount of 5-500 micromol/kg of body weight.

33. A compound according to claim 1, wherein said compound is:
(a) N-(13-carboxy-4-oxo-6,9,12-tris-(carboxylatomethyl)-3,6,9,12-tetraazatridecyl)-3,8-bis(2-hydroxyethyl)-deuteroporphyrin 13-amide, gadolinium complex;

(b) N-(13-carboxy-4-oxo-6,9,12-tris-(carboxylatomethyl)-3,6,9,12-tetraazatridecyl)-3,8-bis(2-hydroxyethyl)-deuteroporphyrin 13-amide, dysprosium complex;
(c) N-(17-carboxy-8-oxo-10,13,16-tris-(carboxylatomethyl)-7,10,13,16-tetraazaheptadecyl)-hematoporphyrin IX 13-amide, gadolinium complex;
(d) N-{5,6-bis[9-carboxy-2,5,8-tris-(carboxylatomethyl)-2,5,8-triazanonylcarbonylamino]-4-oxo-3-azahexyl}-hematoporphyrin IX 13-amide, digadolinium complex;
(e) N,N'-bis-{5,6-bis-[9-carboxy-2,5,8-tris(carboxylatomethyl)-2,5,8-triazanonylcarbonylamino]-4-oxo-3-azahexyl}-hematoporphyrin IX 13,17-diamide, tetragadolinium complex;
(f) N-{9,10-bis-[9-carboxy-2,5,8-tris-(carboxymethyl)-2,5,8-triazanonylcarbonylamino]-8-oxo-7-azadecyl}-hematoporphyrin IX 13-amide, gadolinium complex;
(g) N,N'-(17-carboxy-8-oxo-10,13,16-tris-(carboxylatomethyl)-7,10,13,16-tetraazaheptadecyl)-hematoporphyrin IX 13,17-diamide, digadolinium complex;
(h) N,N'-bis-(13-carboxy-4-oxo-6,9,12-tris-(carboxylatomethyl)-3,6,9,12-tetraazatridecyl)-hematoporphyrin IX 13,17-diamide, digadolinium complex;
(i) N,N'-bis [10-ethoxycarbonyl-3,6,9-tris-(carboxylatomethyl)-3,6,9-triazadecanoylamino]-3,8-bis-(1-methoxyethyl)-deuteroporphyrin 13,17-diamide, gadolinium complex.

34. A method according to claim 20, wherein said compound is:
(a) N-(13-carboxy-4-oxo-6,9,12-tris-(carboxylatomethyl)-3,6,9,12-tetraazatridecyl)-3,8-bis(2-hydroxyethyl)-deuteroporphyrin 13-amide, gadolinium complex;
(b) N-(13-carboxy-4-oxo-6,9,12-tris-(carboxylatomethyl)-3,6,9,12-tetraazatridecyl)-3,8-bis(2-hydroxyethyl)-deuteroporphyrin 13-amide, dysprosium complex;
(c) N-(17-carboxy-8-oxo-10,13,16-tris-(carboxylatomethyl)-7,10,13,16-tetraazaheptadecyl)-hematoporphyrin IX 13-amide, gadolinium complex;
(d) N-{5,6-bis[9-carboxy-2,5,8-tris-(carboxylatomethyl)-2,5,8-triazanonylcarbonylamino]-4-oxo-3-azahexyl}-hematoporphyrin IX 13-amide, digadolinium complex;
(e) N,N'-bis-{5,6-bis-[9-carboxy-2,5,8-tris(carboxylatomethyl)-2,5,8-triazanonylcarbonylamino]-4-oxo-3-azahexyl}-hematoporphyrin IX 13,17-diamide, tetragadolinium complex;
(f) N-{9,10-bis-[9-carboxy-2,5,8-tris-(carboxymethyl)-2,5,8-triazanonylcarbonylamino]-8-oxo-7-azadecyl}-hematoporphyrin IX 13-amide, gadolinium complex;
(g) N,N'-(17-carboxy-8-oxo-10,13,16-tris-(carboxylatomethyl)-7,10,13,16-tetraazaheptadecyl)-hematoporphyrin IX 13,17-diamide, digadolinium complex;
(h) N,N'-bis-(13-carboxy-4-oxo-6,9,12-tris-(carboxylatomethyl)-3,6,9,12-tetraazatridecyl)-hematoporphyrin IX 13,17-diamide, digadolinium complex;
(i) N,N'-bis [10-ethoxycarbonyl-3,6,9-tris-(carboxylatomethyl)-3,6,9-triazadecanoylamino]-3,8-bis-(1-methoxyethyl)-deuteroporphyrin 13,17-diamide, gadolinium complex.

* * * * *